(12) United States Patent
Vakharia et al.

(10) Patent No.: US 10,603,123 B2
(45) Date of Patent: *Mar. 31, 2020

(54) USER INPUT DEVICE FOR ROBOTIC SURGICAL SYSTEM

(71) Applicant: Ethicon LLC, Guaynabo, PR (US)

(72) Inventors: Omar J. Vakharia, Cincinnati, OH (US); James G. Lee, Raynham, MA (US); Matthew S. Corbin, Loveland, OH (US); Mark D. Overmyer, Cincinnati, OH (US); Cory G. Kimball, Hamilton, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/108,966

(22) Filed: Aug. 22, 2018

(65) Prior Publication Data

US 2019/0069960 A1  Mar. 7, 2019

Related U.S. Application Data

(63) Continuation of application No. 15/282,243, filed on Sep. 30, 2016, now Pat. No. 10,085,810.

(Continued)

(51) Int. Cl.
*A61B 34/30* (2016.01)
*A61B 34/00* (2016.01)
(Continued)

(52) U.S. Cl.
CPC ........ *A61B 34/30* (2016.02); *A61B 17/07207* (2013.01); *A61B 18/1445* (2013.01);
(Continued)

(58) Field of Classification Search
CPC ... A61B 34/30; A61B 34/74; A61B 17/07207; A61B 18/1445; A61B 2017/320097;
(Continued)

(56) References Cited

U.S. PATENT DOCUMENTS

| 6,783,524 | B2 | 8/2004 | Anderson et al. |
| 7,789,875 | B2 * | 9/2010 | Brock ............. A61B 34/20 600/424 |

(Continued)

OTHER PUBLICATIONS

U.S. Appl. No. 62/236,356, entitled "User Input Device (UID) and Guided User Interface (GUI) for a Robotic Surgical System," filed Oct. 2, 2015.

*Primary Examiner* — Jaime Figueroa
(74) *Attorney, Agent, or Firm* — Frost Brown Todd LLC

(57) ABSTRACT

A robotic surgical system includes a robotic surgical assembly and a control assembly. The robotic surgical assembly includes a robotic actuation assembly, a processing device, and a first communication device. The robotic actuation assembly includes a robotic arm. The processing device is configured to instruct the robotic actuation assembly to perform a task based on a set of instructions. The first communication device is operable to transfer the set of instructions to the processing device. The control assembly includes a second communication device and a user input device. The second communication device is operable to communicate the set of instructions to the first communication device. The user input device assembly is configured to generate the set of instructions and send the set of instruction to the second communication device. At least a portion of the instructions are based on positioning of the user input device within three-dimensional space.

20 Claims, 24 Drawing Sheets

Related U.S. Application Data

(60) Provisional application No. 62/236,356, filed on Oct. 2, 2015.

(51) Int. Cl.
*A61B 18/14* (2006.01)
*B25J 13/02* (2006.01)
*B25J 13/00* (2006.01)
*A61B 17/072* (2006.01)
*B25J 13/08* (2006.01)
*A61B 17/32* (2006.01)
*A61B 17/00* (2006.01)
*A61B 90/00* (2016.01)
*A61B 34/20* (2016.01)

(52) U.S. Cl.
CPC ............ *A61B 34/74* (2016.02); *B25J 13/006* (2013.01); *B25J 13/02* (2013.01); *B25J 13/089* (2013.01); *A61B 2017/00212* (2013.01); *A61B 2017/00438* (2013.01); *A61B 2017/320097* (2017.08); *A61B 2034/2048* (2016.02); *A61B 2034/2051* (2016.02); *A61B 2034/2055* (2016.02); *A61B 2090/372* (2016.02)

(58) Field of Classification Search
CPC .......... A61B 2017/00438; A61B 2017/00212; A61B 2090/372; A61B 2034/2048; A61B 2034/2051; A61B 2034/2055; B25J 13/089; B25J 13/006; B25J 13/02
USPC .................................. 700/245, 257
See application file for complete search history.

(56) References Cited

U.S. PATENT DOCUMENTS

| | | | |
|---|---|---|---|
| 8,670,816 B2 | 3/2014 | Green et al. | |
| 8,768,516 B2 | 7/2014 | Diolaiti et al. | |
| 8,989,528 B2 | 3/2015 | Udd | |
| 9,084,623 B2 | 7/2015 | Gomez et al. | |
| 9,579,088 B2 | 2/2017 | Farritor et al. | |
| 9,770,174 B2 | 9/2017 | Islam | |
| 9,962,158 B2 | 5/2018 | Hall et al. | |
| 9,962,179 B2 | 5/2018 | Castro et al. | |
| 10,052,164 B2 | 8/2018 | Overmyer | |
| 10,085,810 B2 | 10/2018 | Vakharia et al. | |
| 2003/0182091 A1 | 9/2003 | Kukuk | |
| 2006/0178559 A1* | 8/2006 | Kumar | A61B 34/37 600/109 |
| 2007/0088340 A1 | 4/2007 | Brock et al. | |
| 2010/0225209 A1 | 9/2010 | Goldberg et al. | |
| 2010/0332033 A1 | 12/2010 | Diolaiti et al. | |
| 2011/0040305 A1 | 2/2011 | Gomez et al. | |
| 2012/0078080 A1 | 3/2012 | Foley et al. | |
| 2012/0184955 A1 | 7/2012 | Pivotto et al. | |
| 2012/0310221 A1* | 12/2012 | Durant | A61B 34/71 606/1 |
| 2014/0039681 A1 | 2/2014 | Bowling et al. | |
| 2014/0156074 A1 | 6/2014 | Seo et al. | |
| 2014/0222207 A1 | 8/2014 | Bowling et al. | |
| 2015/0094653 A1 | 4/2015 | Pacheco et al. | |
| 2015/0157411 A1* | 6/2015 | Choi | A61B 34/30 606/130 |
| 2015/0374446 A1 | 12/2015 | Malackowski et al. | |
| 2016/0081753 A1* | 3/2016 | Kostrzewski | A61B 34/25 606/130 |

\* cited by examiner

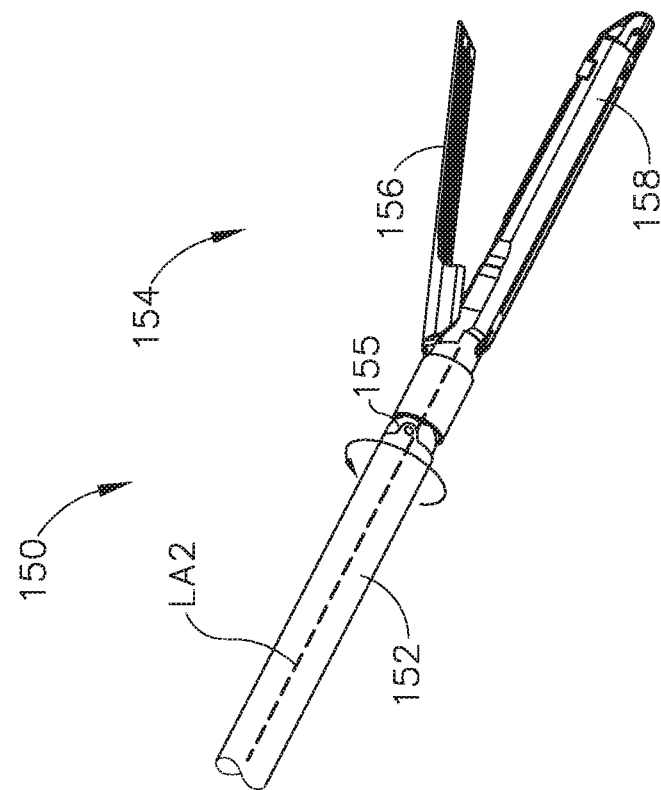
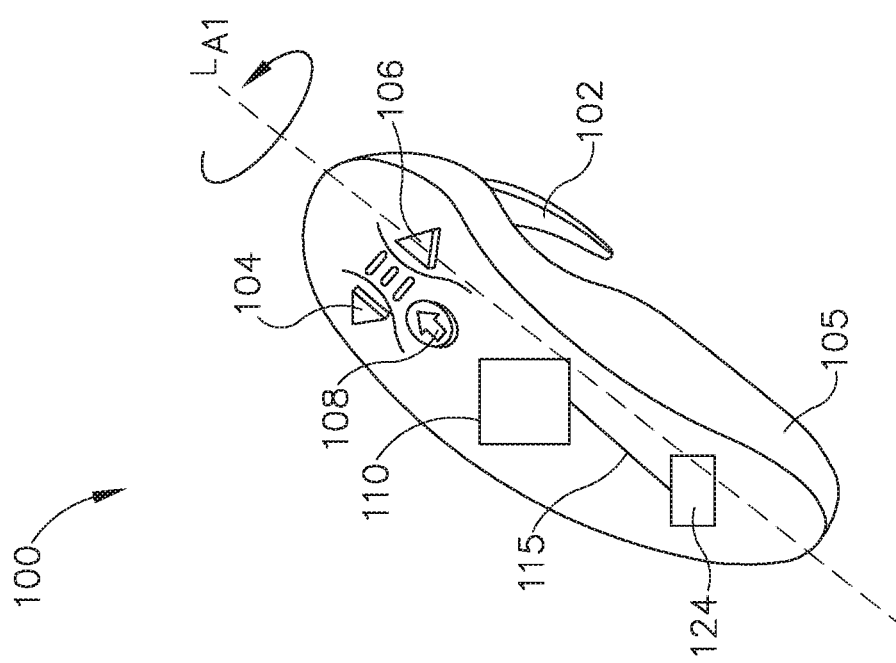

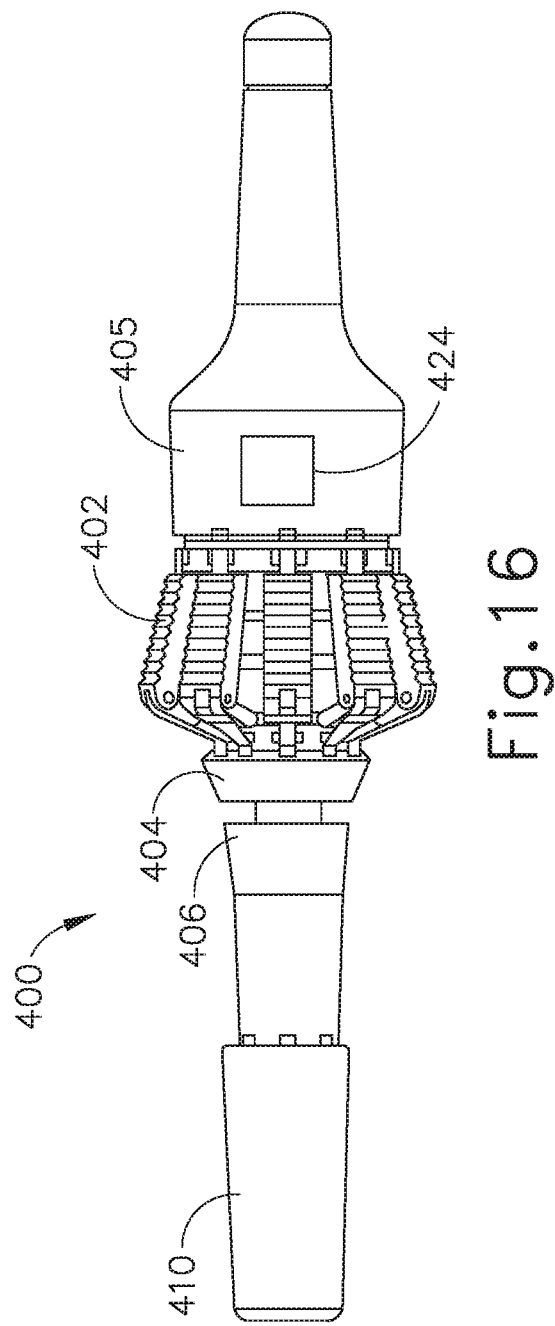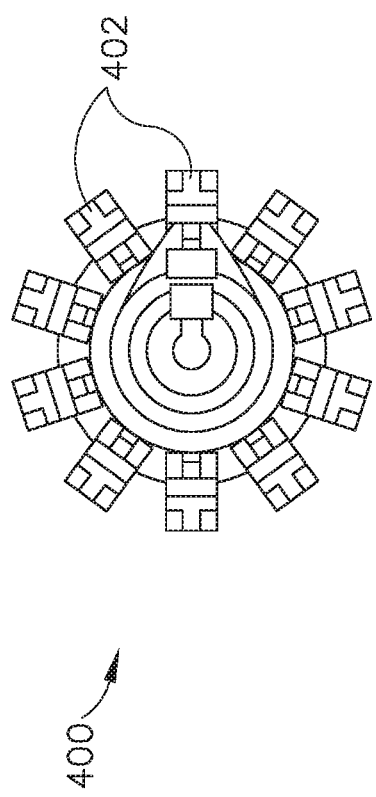

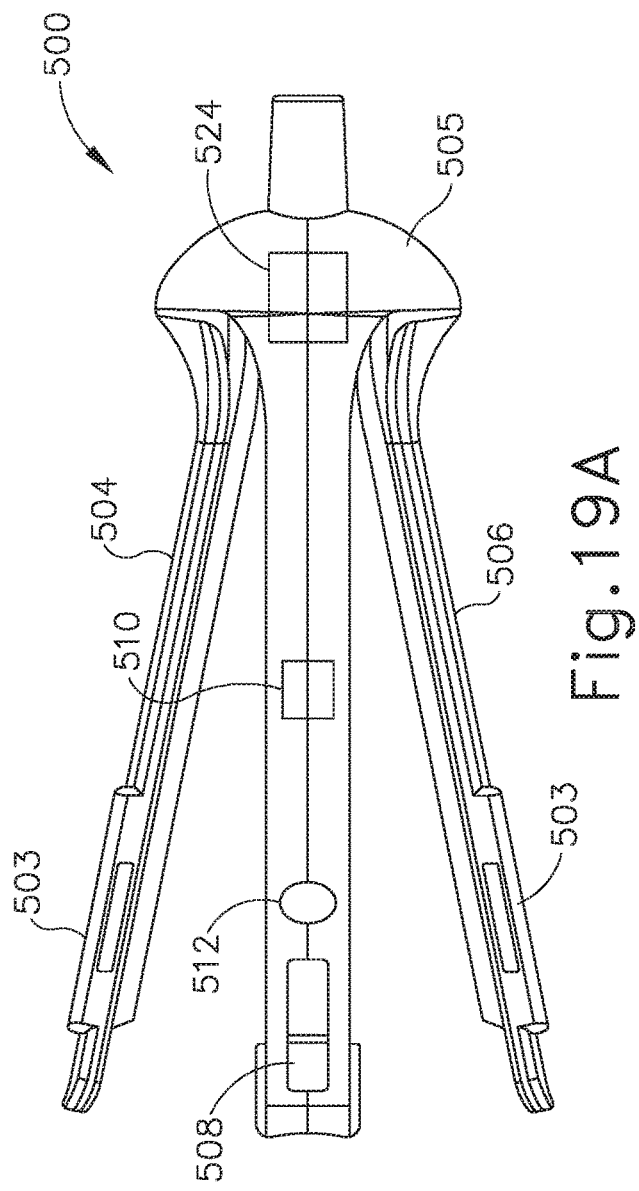
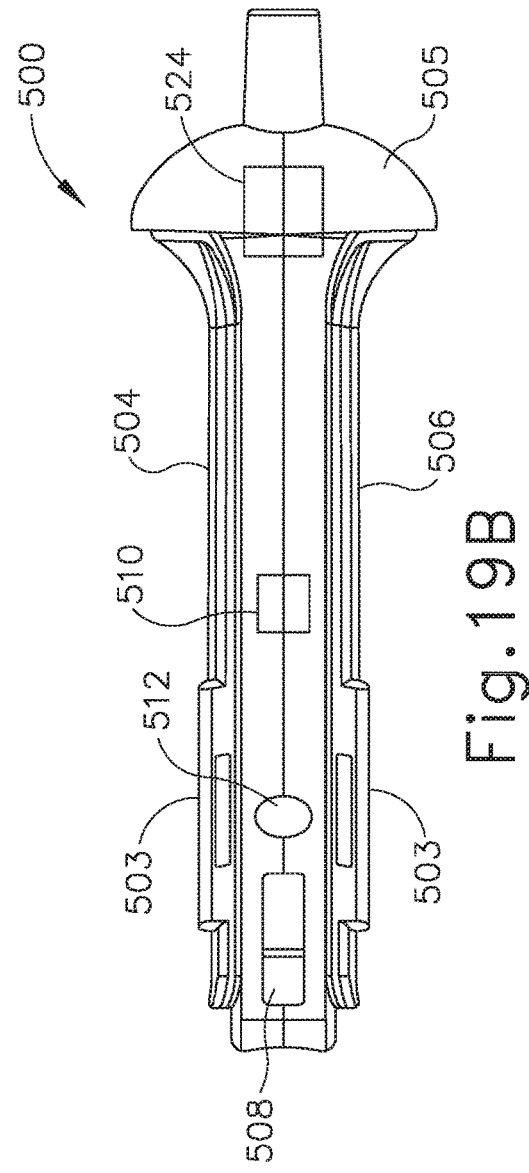
Fig. 19A
Fig. 19B

USER INPUT DEVICE FOR ROBOTIC SURGICAL SYSTEM

PRIORITY

This application is a continuation of U.S. patent application Ser. No. 15/282,243, entitled "User Input Device for Robotic Surgical System," filed Sep. 30, 2016, now U.S. Pat. No. 10,085,810, issued Oct. 2, 2018, which claims priority to U.S. Provisional Patent App. No. 62/236,356, entitled "User Input Device (UID) and Guided User Interface (GUI) for a Robotic Surgical System," filed Oct. 2, 2015.

BACKGROUND

Robotic controls may be used in a wide variety of surgical procedures. For example, in minimally invasive robotic surgery, surgical operations may be performed through a small incision in the patient's body. In addition to a wide variety of surgical procedures, a robotic surgical system may be used with various types of surgical instruments, including but not limited to surgical staplers, ultrasonic instruments, electrosurgical instruments, suturing instruments, and/or various other kinds of instruments.

A robotic surgical system may include an operation assembly and a control assembly, which may be positioned in separate locations. An operation assembly may include various cameras and robotic arms configured to operate on a patient. Cameras may be used to capture desired images of a patient and robotic arms during a procedure. Robotic arms may connect to and manipulate various compatible surgical equipment in order to physically perform a surgical procedure. A control assembly may include a viewing screen and various user input devices. The viewing screen may be used to view images provided by the cameras of the operation assembly. The user input devices may be used in order to manipulate the robotic arms and the compatible surgical equipment attached to the robotic arms. In other words, an operator may remotely perform a surgical procedure with the user input devices of the control assembly and the robotic arms of the operation assembly, while simultaneously viewing the surgical procedure with the cameras of the operation assembly and the viewing screen of the control assembly.

In some robotic surgical systems, the user input devices are physically attached to the rest of the control assembly. Therefore, while the robotic arms may connect to and manipulate various compatible surgical equipment, the same user input devices must be used in order to control various surgical equipment attached to the robotic arms.

While various kinds of robotic surgical systems and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4 depicts a perspective view of the user input device of FIG. 2, where the user input device is rotated about its own longitudinal axis;

FIG. 5 depicts a perspective view of the portion of the surgical instrument of FIG. 3, where the surgical instrument is rotated about its own longitudinal axis in response to the rotational movement shown in FIG. 4 of the user input device of FIG. 2.

FIG. 16 depicts a side elevational view of the user input device of FIG. 15A, where the activation buttons are in the open configuration;

FIG. 17 depicts a front elevational view of the user input device of FIG. 15A;

FIG. 19A depicts a top plan view of the user input device of FIG. 18, where the moving actuators are in the open configuration;

FIG. 19B depicts a top plan view of the user input device of FIG. 18, where the moving actuators are in a closed configuration;

Figure 1:
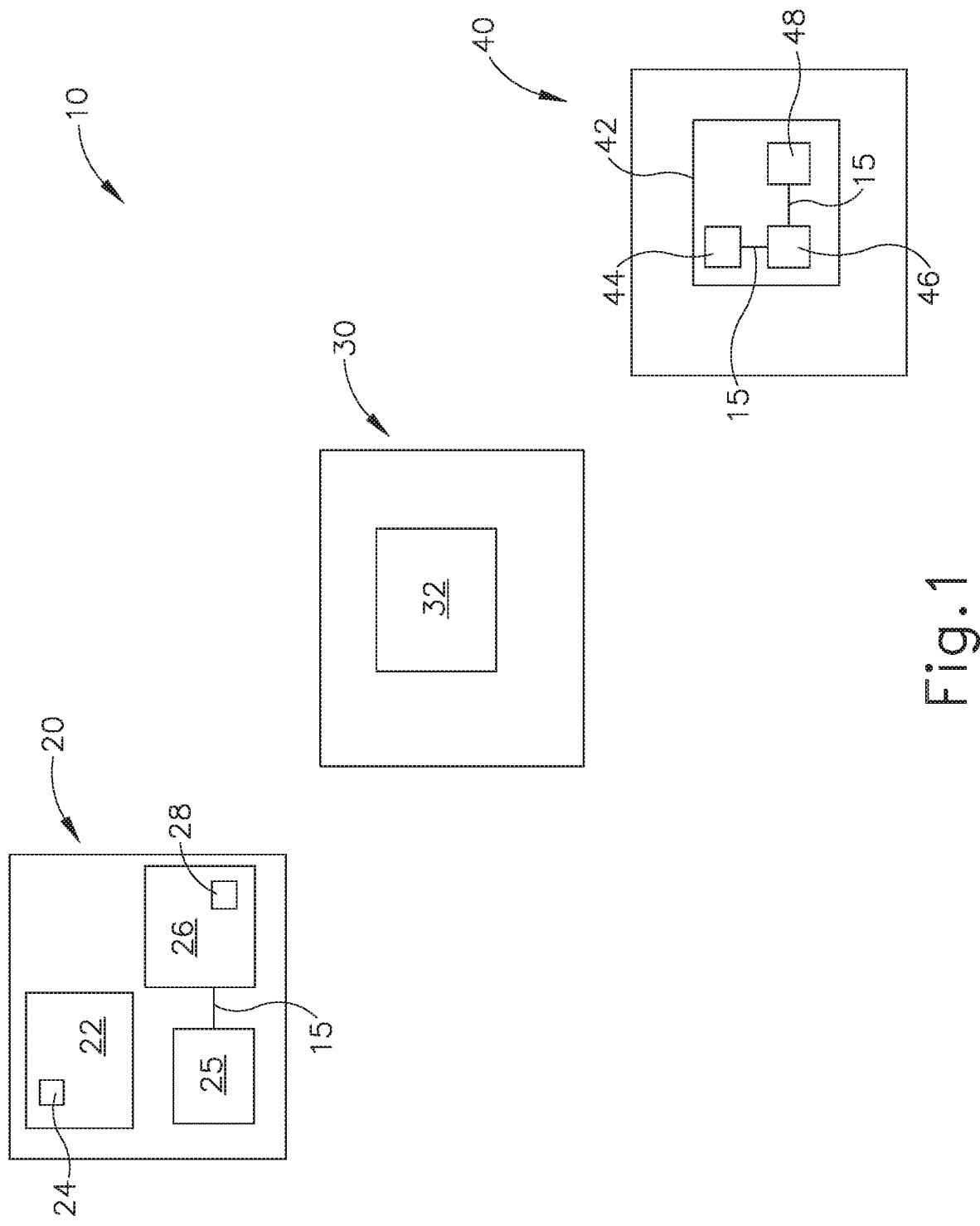
FIG. 1 depicts a schematic diagram of an exemplary robotic surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Exemplary Robotic Surgical System

FIG. 1 shows a schematic diagram of an exemplary robotic surgical system (10).

Robotic surgical system (10) includes an exemplary control assembly (20), an exemplary data transmission unit (30), and an exemplary operation assembly (40). As will be described in greater detail below, control assembly (20) is configured generate commands that are used to actuate operation assembly (40) to perform a desired surgical procedure.

Operation assembly (40) includes a robotic surgical assembly (42) that is configured to operate on a patient. Robotic surgical assembly (42) includes a communication device (44), a processing device (46), and a robotic actuation assembly (48). Robotic actuation assembly (48) may include one or multiple movable robotic arms that are attached to various surgical instruments, such as surgical staplers, ultrasonic surgical instruments, electrosurgical instruments, suturing instruments, endoscopic cameras, sensors, and/or various other kinds of instruments that would be apparent to one having ordinary skill in the art in view of the teachings herein. Additionally, robotic arms may actuate, articulate, control, and/or activate corresponding attached surgical instruments in any suitable manner that would be apparent to one having ordinary skill in the art in view of the teachings herein. As will be described in greater detail below, control assembly (20) may control functions of robotic actuation assembly (48), such as movement of robotic arms and control of attached surgical instruments.

in the present example, robotic actuation assembly (48) is in communication with processing device (46) via communication wire (15), though this communication may be provided wirelessly if desired. Processing device (46) is operable to instruct robotic actuation assembly (48) on precise movements and actions of the robotic arms and surgical instruments that are attached to the robotic arms. Additionally, sensors, endoscopic cameras, and other suitable instrumentation of robotic actuation assembly (48) may provide feedback information to processing device (46).

Processing device (46) is also in communication with communication device (44) via communication wire (15), though again this communication may be wireless in some versions. Communication device (44) establishes communication between data transmission unit (30) and processing device (46). Processing device (46) is operable to receive instructions from transmission unit (30) via communication device (44). Processing device (46) may further interpret those instructions and transmit them to robotic actuation assembly (48). Therefore, robotic actuation assembly (48) may move robotic arms and move, articulate, control, and/or activate attached surgical instruments in response to transmitted instructions from data transmission unit (30) to robotic actuation assembly (48) via communication device (44). Communication device (44) may also transfer data from processing device (46) to data transmission unit (30), such as data from sensors or endoscopic cameras within robotic actuation assembly (48).

Data transmission unit (30) includes a server (32), which may receive, store, and transmit information to and from operation assembly (40), as described above, and exemplary control assembly (20), as will be described in greater detail below. In other words, server (32) may act as an intermediary between control assembly (20) and operation assembly (40). In some versions, server (32) may also store at least some of the communications between control assembly (20) and operation assembly (40). Server (32) may utilize any suitable means of receiving, storing, and transmitting information as would be apparent to one having ordinary skill in the art in view of the teachings herein. It should be understood that storing information on server (32) is merely optional. Therefore, server (32) may strictly act as an intermediary between control assembly (20) and operation assembly (40). It should also be understood that control assembly (20) and operation assembly (40) may be coupled with server (32) using any known networking components and techniques. Moreover, in some versions, control assembly (20) and operation assembly (40) are in direct communication with each other, such that data transmission unit (30) may simply be omitted.

Control assembly (20) includes a user input device assembly (22) containing a first wireless communication device (24), a processing device (26) containing a second wireless communication device (28), and an exemplary viewing screen (25) in communication with processing device (26) via a communication wire (15) (though again this coupling may be wireless if desired). As will be described in greater detail below, user input device assembly (22) may instruct robotic actuation assembly (48) to move and/or activate as described above.

User input device assembly (22) is physically separated from processing device (26). Therefore, user input device assembly (22) may be freely moved relative to the rest of control assembly (20), provided that a communication link is maintained between wireless communication devices (24, 28). User input device assembly (22) is configured to be grasped by an operator in order to generate control signals, which are sent to first wireless communication device (24). First wireless communication device (24) is in communication with second wireless communication device (28) such that control signals may be sent from user input device assembly (22) to second wireless communication device (28). Additionally, second wireless communication device (28) may also send information to first wireless communication device (28).

Second wireless communication device (28) may selectively establish communication with first wireless communication device (24). By way of example only, wireless communication devices (24, 28) may communicate with each other using Bluetooth or any other suitable protocol or modality. Registration of user input device assembly with processing device (26) may be achieved through a digital handshake or any other suitable method that would be apparent to one having ordinary skill in the art in view of the teachings herein. Therefore, multiple or different user input device assemblies (22) may be utilized with the rest of control assembly (20). In other words, user input device assemblies (22) may be switched out for alternative user input device assemblies (22) depending on the preference of an operator. It should also be understood that various kinds of user input device assemblies (22) may be used by a single operator within a single surgical procedure. In such scenarios, the various user input device assemblies (22) may simultaneously maintain registration with processing device (26); or user input device assemblies (22) may be serially registered and de-registered with processing device (26), such that only one user input device assemblies (22) is registered with processing device (26) at a given moment during a surgical procedure. Other suitable registration and communication scenarios will be apparent to those of ordinary skill in the art in view of the teachings herein.

Second wireless communication device (28) is also in communication with both processing device (26) and data transmission unit (30). Therefore, second wireless communication device (28) may send control signals received from first wireless communication device (24) to both processing device (26) and server (32) of data transmission unit (30). As mentioned above, data transmission unit (30) is also in communication with processing device (46) of robotic assembly (42) via communication device (44). Processing device (46) may control movement of robotic actuation assembly (48). Therefore, control signals generated by user input device assembly (22) may control robotic actuation assembly (48) via wireless communication devices (24, 28), first processing device (26), server (32), communication device (44), and second processing device (46).

Second wireless communication device (28) may also receive information from data transmission unit (30). As mentioned above, data transmission unit (30) may receive data from sensors, endoscopic cameras, other suitable instrumentation of robotic actuation assembly, or any other information generated by operation assembly (40). Therefore, second wireless communication device (28) may send processing unit (26) information from operation assembly (40), which may be interpreted and processed by processing device (26) and displayed on viewing screen (25) and/or user input device assembly (22).

While in the current example, user input device assembly (22) is in wireless communication with processing device (26), any other suitable communication means may be used as would be apparent to one having ordinary skill in the art in view of the teachings herein. For example, a communication wire (15) may connect processing device (26) and user input device assembly (22).

In exemplary use, an operator may be located at control assembly (20) while a patient is located at operation assembly (40). The operator may view live images generated by endoscopic cameras of robotic actuation assembly (48) on viewing screen (25) and/or other cameras within operation assembly (40). While viewing live images generated by endoscopic cameras of robotic actuation assembly (48), the operator may grasp and manipulate user input device assembly (22) and thereby generate desired control signals, which in turn instruct surgical instruments of robotic actuation assembly (48) to operate on the patient.

It should be understood that control assembly (20), data transmission unit (30), and operation assembly (40) may all be located at different locations. Alternatively, any suitable combination of control assembly (20), data transmission unit (30), and operation assembly may be located at the same location as would be apparent to one having ordinary skill in the art in view of the teachings herein. For example, control assembly (20) and data transmission unit (30) may be located in a first building, while operation assembly (40) may be located at a second building miles away. Additionally, data transmission unit (30) may be incorporated into portions of control assembly (20) and/or operation assembly (40).

It should also be understood that since control assembly (20) may be located at a difference location than an operator, an operator may manipulate operation assembly (40) while stationed at a different location. For instance, in some scenarios, the operator and the patient are hundreds or thousands of miles apart from each other during the surgical procedure. In some other scenarios, the operator and the patient are on the same campus or in the same building but are in separate rooms from each other. In still other scenarios, the operator and the patient are in the same room as each other. Other suitable scenarios relating to operator-patient positioning will be apparent to those of ordinary skill in the art in view of the teachings herein.

II. Exemplary User Input Device Assemblies and Surgical Instruments

In some instances, it may be desirable to have a control assembly (20) with an intuitive user input device. A more intuitive user input device may be more similar in size, dimensions, and functionality to a traditional surgical instrument. Providing an intuitive user input device may be beneficial in that it may take less training time for an operator to become familiar with a robotic surgical system (10). The following describes various examples of intuitive user input devices that may be used to form part of user input device assembly (22) of robotic surgical system (10).

A. Egg Shaped User Input Device and Exemplary Surgical Instrument

FIGS. 2-9 show an exemplary user input device (100) being used to control an exemplary surgical instrument (150). User input device (100) may be readily incorporated into control assembly (20) of robotic surgical system (10) as a version of user input device assembly (22) described above. Surgical instrument (150) may be readily incorporated into robotic actuation assembly (48) of robotic assembly (42) described above. In particular, surgical instrument (150) may be attached to a robotic arm such that robotic arm may actuate, articulate, and activate surgical instrument (150); and such that movement of robotic arm moves surgical instalment (150).

In the present example, surgical instrument (150) includes a longitudinal shaft (152) connected to an end effector (154) at an articulation joint (155). End effector (154) is configured to articulate relative to the longitudinal axis (LA2) defined by shaft (152) at articulation joint (155). End effector (154) includes a first jaw (156) and a second jaw (158). First jaw (156) is configured to pivot from an open position to a closed position relative to second jaw (158). End effector (154) may be used to grasp and manipulate tissue. End effector (154) may be configured to operate on tissue in a variety of ways as would be apparent to one having ordinary skill in the art in view of the teachings herein. For example, end effector (154) may include a surgical stapling and cutting assembly, an ultrasonic blade with a clamp arm, a set of RF electrodes and a cutting blade, a suturing assembly, and/or various other kinds of end effectors. It should be understood that various features of surgical instrument (150) or surgical instrument (150) itself may be replaced with other surgical instruments as would be apparent to one having ordinary skill in the art in view of the teachings here.

User input device (100) may include the features of user input device assembly (22) described above, with differences elaborated below. User input device (100) includes a wireless communication device (124), which is substantially similar to wireless communication device (24) described above. Therefore, user input device (100) may selectively communicate with processing device (26) by wireless communication device (124) selectively establishing communication with second wireless communication device (28). Additionally, as will be described in greater detail below, user input device (100) is configured to generate control signals that may be communicated to robotic actuation assembly (48) in order to move and/or activate surgical instrument (150).

User input device (100) also includes an egg-shaped body (105), a pivoting trigger (102), a pair of articulation buttons (104, 106), an activation button (108), and a position sensing assembly (110). Egg-shaped body (105) is dimensioned to be grasped. by an operator with one hand such that the index finger is adjacent to trigger (102) and the thumb of the same hand is adjacent to articulation buttons (104, 106) and activation button (108). As will be described in greater detail below, trigger (102), articulation buttons (104, 106), activation button (108), and position sensing assembly (110) are all configured to generate control signals that control surgical instrument (150). Moreover, trigger (102), articulation buttons (104, 106), activation button (108), and position sensing assembly (110) are all in communication with wireless communication device (124). Therefore, wireless communication device (124) may send control signals generated by trigger (102), articulation buttons (104, 106), activation button (108), and. position sensing assembly (110) to processing device (26), which may then be communicated to robotic actuation assembly (48) as previously described above in order control surgical instrument (150).

Figure 2:
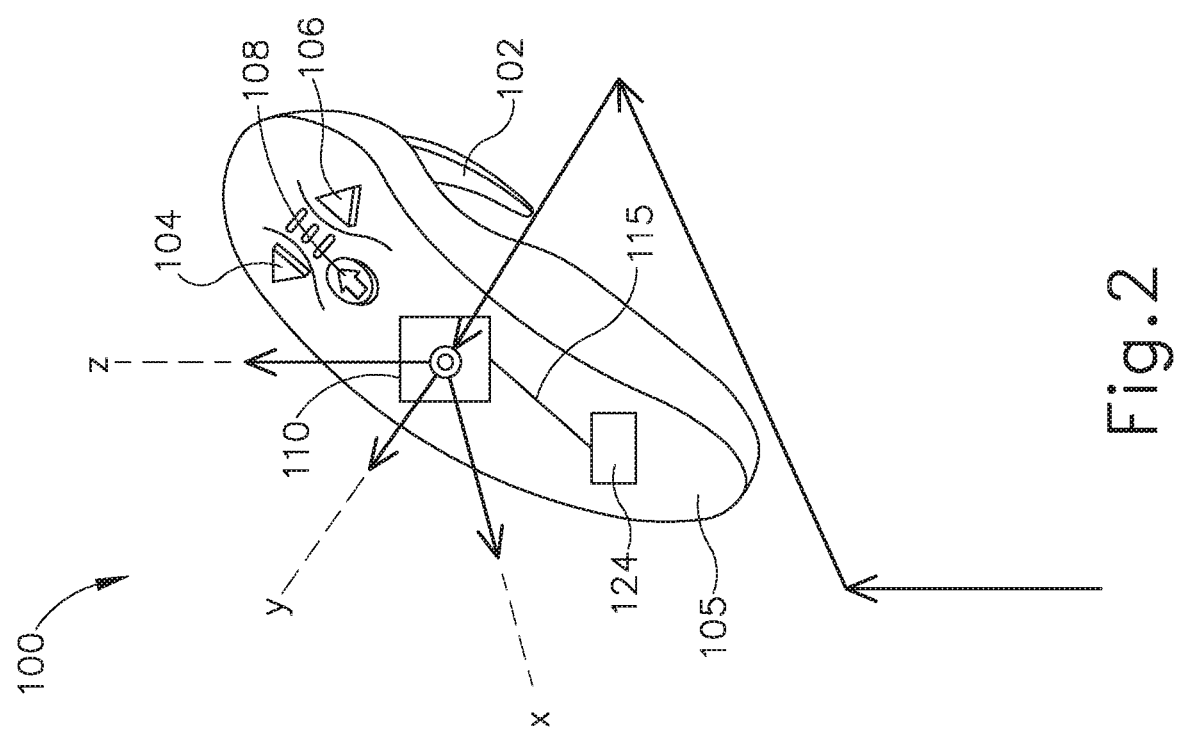
FIG. 2 depicts a perspective view of an exemplary user input device that may be readily incorporated into the robotic surgical system of FIG. 1, where the user input device is moved in three linear directions.

As best seen in FIGS. 2 and 4, position sensing assembly (110) is configured to determine the spatial location of user input device (100) within a 3-dimensional space. In other words, position sensing assembly (110) is configured to determine the axial location of user input device (100) along the X axis (X), Y axis (Y), and Z axis (Z). Position sensing assembly (110) is also configured to determine the rotational position of user input device (100) about the longitudinal axis (LA1) of body (105). In addition, or in the alternative, position sensing assembly (110) may determine the rotational position of user input device about each of the X axis (X), Y axis (Y), and Z axis (Z). Position sensing assembly (110) may thus provide position data relative to up to six dimensions. As best seen in FIG. 2, as body (105) is translated along the X axis (X), Y axis (Y), and Z axis (Z), position sensing assembly (110) generates a set of control signals corresponding to the axial translation. Control signals may be sent to wireless communication device (124) via communication wire (115) or any other suitable means as would be apparent to one having ordinary skill in the art in view of the teachings herein. Control signals corresponding to the translation of body (105) along axes (X, Y, Z) may then be communicated to robotic actuation assembly (48) via wireless communication devices (124, 28), first processing device (26), server (32), communication device (44), and second processing device (46) as described above.

Figure 3:
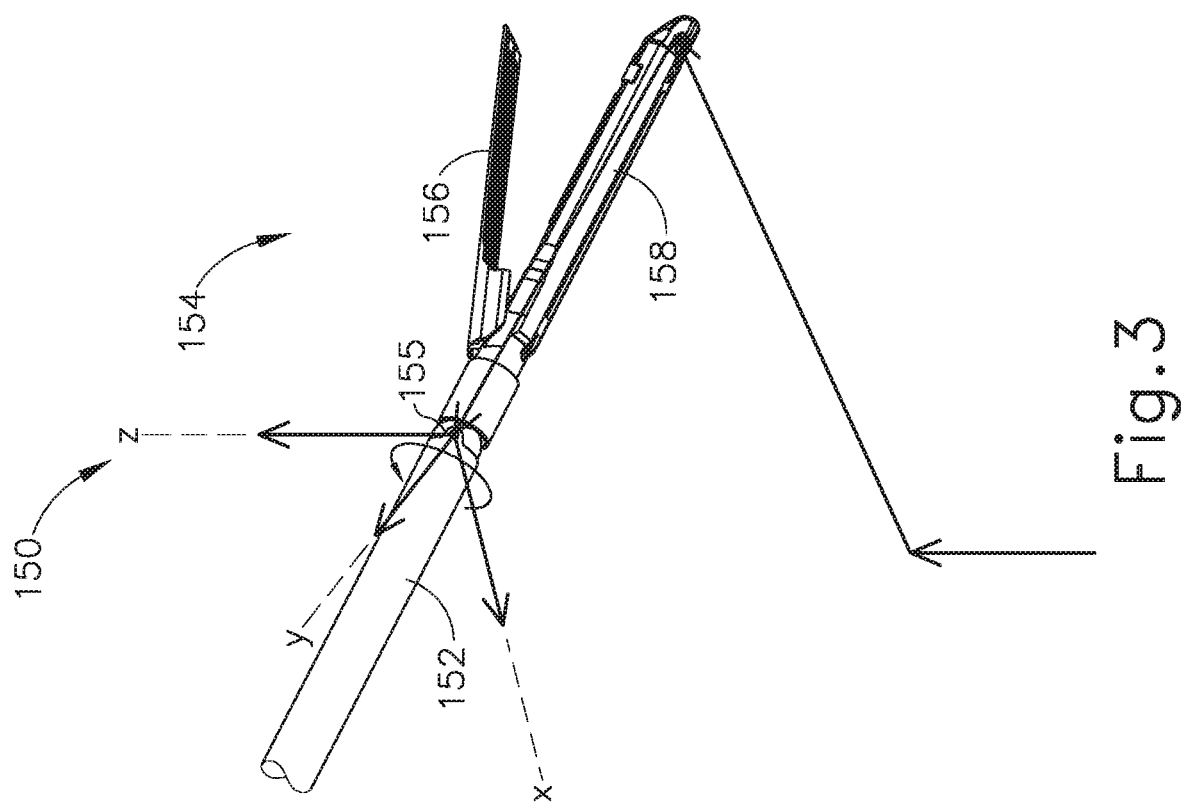
FIG. 3 depicts a perspective view of a portion of an exemplary surgical instrument that may be readily incorporated into the robotic surgical system of FIG. 1, where the surgical instrument is moved in three linear directions in response to the linear movement shown in FIG. 2 of the user input device of FIG. 2.

As best seen in FIG. 3, robotic actuation assembly (48) may receive corresponding control signals and then move the robotic arm attached to surgical instrument (150) so that surgical instrument (150) translates along axes (X, Y, Z) to mimic movement of user input device (100). In some versions, such mimicked movement by surgical instrument (150) is in a 1:1 proportion to the movement of user input device (100). In some other versions, the movement of surgical instrument (150) is reduced or enhanced in magnitude relative to the corresponding movement of user input device (100). Regardless of the relationship between the movement of user input device and the resulting movement of surgical instrument (150), it should be understood that an operator may simultaneously view the corresponding movement of surgical instrument (150) via an endoscopic camera communicating live video images to viewing screen (25). Therefore, an operator may adjust the movement of user input device (100) based on visual feedback provided by robotic actuation assembly (48).

As best seen in FIG. 4, as body (100) is rotated about the longitudinal axis (LA1) of body (105), position sensing assembly (110) generates a set of control signals corresponding to the rotation. Control signals may be sent to wireless communication device (124) via communication wire (115) or any other suitable means as would be apparent to one having ordinary skill in the art in view of the teachings herein. Control signals corresponding to the rotation of body (105) about its longitudinal axis (LA1) may then be communicated to robotic actuation assembly (48) via wireless communication devices (124, 128), first processing device (26), server (32), communication device (44), and second processing device (46) as described above. As best seen in FIG. 5, robotic actuation assembly (40) may receive corresponding control signals and then move the robotic arm attached to surgical instrument (150) so that surgical instrument (150) rotates about longitudinal axis (LA2) defined by shaft assembly (152) to mimic movement of user input device (100). Again, this mimicked movement by surgical instrument (150) may be in 1:1 proportion to the movement of user input device (100) or have any other suitable relationship with the movement of user input device (100). It should be understood that an operator may simultaneously view the corresponding movement of surgical instrument (150) via an endoscopic camera communicating live video images to viewing screen (25). Therefore, an operator may adjust the movement of user input device (100) based on visual feedback provided by robotic actuation assembly (48).

Position sensing assembly (110) may determine the position of user input device (100) through any suitable means as would be apparent to one having ordinary skill in the art in view of the teachings herein. As a merely illustrative example, position sensing assembly (110) may include a one or more accelerometers that configured to sense movement of user input device (100) to generate a control signal. In another merely illustrative example, position sensing assembly (110) may include a metallic coil located within body (105) of user input device (100), while the area in which user input device (100) is located is within an electromagnetic field. The movement of user input device (100) within the electromagnetic field may generate a specific current within the metallic coil in body (105), and this current generated in the coil may be used to determine the location of the metallic coil within the electromagnetic field. This information may be used to generate a position based control signal. As another merely illustrative example, position sensing assembly (110) may include one or more optical markers on body (105), with user input device (100) being used within the field of view of one or more cameras or optical sensors that track movement of the optical markers on body (105) to determine the location and orientation of user input device (100) within a controlled space. Other suitable components and techniques that may be used to provide position sensing assembly (110) will be apparent to those skilled in the art in view of the teachings herein. It should also be understood that combinations of components and techniques may be used to provide position sensing assembly (110) (e.g., a combination of accelerometers and optical sensing, etc.).

As noted above, corresponding movement of surgical instrument (150) in response to control signals generated by movement of user input device (100) may be at a 1:1 ratio such that for every unit of measurement moved by user input device (100), surgical instrument (150) also moves the same unit of measurement in along the corresponding axis (X, Y, Z, LA2). However, any movement ratio may be used as would be apparent to one having ordinary skill in the art in view of the teachings herein. For example, for every 3 units of measurement moved by user input device (100), surgical instrument (150) may move one unit of measurement. This may give an operator greater control of surgical instrument (150) as compared to a movement ratio of 1:1.

Figure 7:
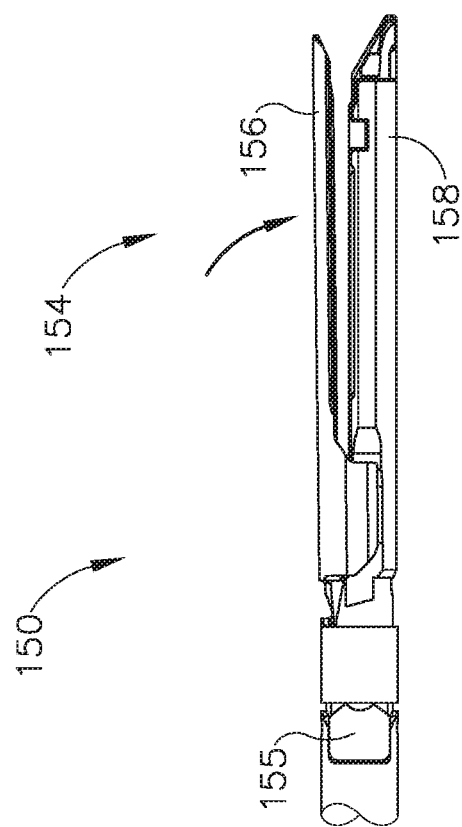
FIG. 7 depicts a side elevational view of the portion of the surgical instrument of FIG. 3, where jaws of an end effector of the surgical instrument actuate from an open configuration to a closed configuration in response to actuation of the trigger button shown in FIG. 6 from the open position to the closed position.
Figure 6:
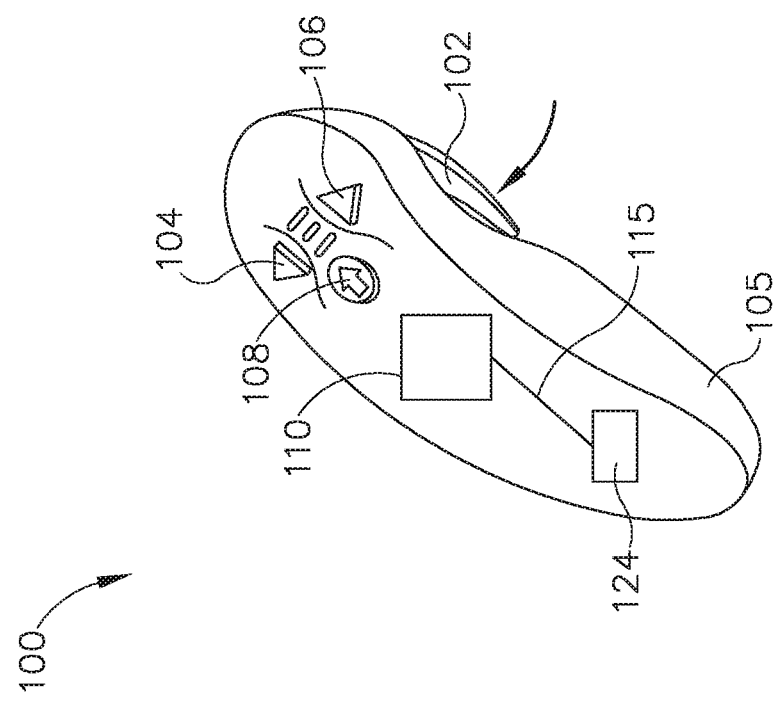
FIG. 6 depicts a perspective view of the user input device of FIG. 2, with a trigger button actuated from an open position to a closed position.

As mentioned above, and as will be described in greater detail below, trigger (102), articulation buttons (104), and activation button (108) are each configured to generate a control signal corresponding with a specific movement/actions of surgical instrument (150). FIGS. 6-7 show trigger (102) being pulled toward body (105) and first jaw (156) closing toward second jaw (158) of end effector (150) in response to this movement of trigger (102). Trigger (102) being pulled toward body (105) thus generates a set of control signals corresponding to jaw (156) closure. Control signals may be sent to wireless communication device (124) via communication wire (115) or any other suitable means as would be apparent to one having ordinary skill in the art in view of the teachings herein. Control signals corresponding to jaw (156) closure may then be communicated to robotic actuation assembly (48) via wireless communication devices (124, 28), first processing device (26), server (32), communication device (44), and second processing device (46) as described above. Robotic actuation assembly (48) may receive corresponding control signals and then close first jaw (156) toward second jaw (158). It should be understood that an operator may simultaneously view the corresponding movement of surgical instrument (150) via an endoscopic camera communicating live video images to viewing screen (25). Therefore, an operator may adjust the movement of user input device (100) based on visual feedback provided by robotic actuation assembly (48).

Figure 9:
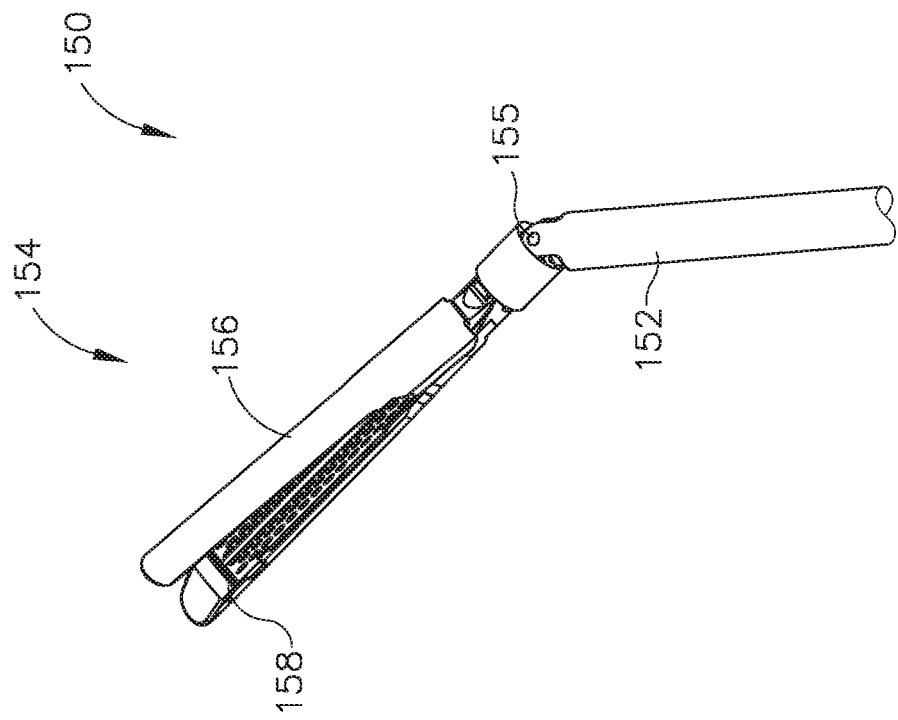
FIG. 9 depicts a perspective view of the portion of the surgical instrument of FIG. 3, where the end effector is moved to an articulated position in relation to the shaft of the surgical instrument in response to activation of the articulation button shown in FIG. 8.
Figure 8:
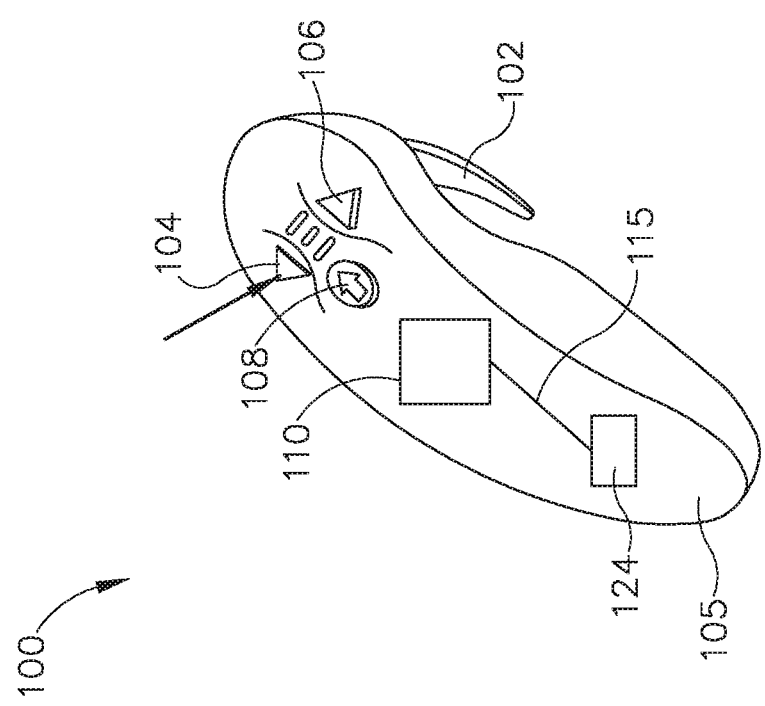
FIG. 8 depicts a perspective view of the user input device of FIG. 2, with an articulation button activated.

FIGS. 8-9 show articulation button (104) being pressed and end effector (154) articulating relative to longitudinal axis (LA2) defined by shaft assembly (152) in response to this pressing of articulation button (104). Articulation button (104) being pressed generates a set of control signals corresponding to articulation of end effector (154) about articulation joint (155) in a first direction. It should be understood that pressing articulation button (106) generates a set of control signals corresponding to articulation of end effector (165) about articulation joint (155) in a second, opposite, direction. Control signals may be sent to wireless communication device (124) via communication wire (115) or any other suitable means as would be apparent to one having ordinary skill in the art in view of the teachings herein. Control signals corresponding to articulation of end effector (154) about articulation joint (155) may then be communicated to robotic actuation assembly (48) via wireless communication devices (124, 28), first processing device (26), server (32), communication device (44), and second processing device (46) as described above. Robotic actuation assembly (48) may receive corresponding control signals and then close first jaw (156) toward second jaw (158). It should be understood that an operator may simultaneously view the corresponding movement of surgical instrument (150) via an endoscopic camera communicating live video images to viewing screen (25). Therefore, an operator may adjust the movement of user input device (100) based on visual feedback provided by robotic actuation assembly (48).

If an operator presses activation button (108), end effector (154) may be activated to manipulate tissue. For instance, in versions where end effector (154) is an endocutter end effector that provides severing and stapling of tissue, end effector (154) would sever tissue captured between jaws (156, 158) and staple the severed tissue in response to the operator pressing activation button (108). Activation button (108) being pressed generates a set of control signals corresponding to activation of end effector (154). Control signals may be sent to wireless communication device (124) via communication wire (115) or any other suitable means as would be apparent to one having ordinary skill in the art in view of the teachings herein. Control signals corresponding to activation of end effector (154) may then be communicated to robotic actuation assembly (48) via wireless communication devices (124, 28), first processing device (26), server (32), communication device (44), and second processing device (46) as described above. Robotic actuation assembly (48) may receive corresponding control signals and then activate end effector (154).

B. Pistol Grip User Input Device with Pincher Actuation

FIGS. 10A-12 show an exemplary alternative user input device (200) that may be readily incorporated into control assembly (20) of robotic surgical system (10) as a version of user input device assembly (22), in place of user input device (100) described above. Therefore, user input device (200) may be used to control surgical instrument (150) or any other surgical instrument incorporated into a robotic arm of robotic actuation assembly (48).

User input device (200) of the present example is configured and operable just like user input device (100) described above, with differences elaborated below. User input device (200) includes a wireless communication device (224), which is substantially similar to wireless communication device (24, 124) described above. Therefore, user input device (200) may selectively communicate with processing device (26) by wireless communication device (224) selectively establishing communication with second wireless communication device (28). Additionally, as will be described in greater detail below, user input device (200) is configured to generate control signals that may be communicated to robotic actuation assembly (48) in order to move and/or activate surgical instrument (150).

Figure 11:
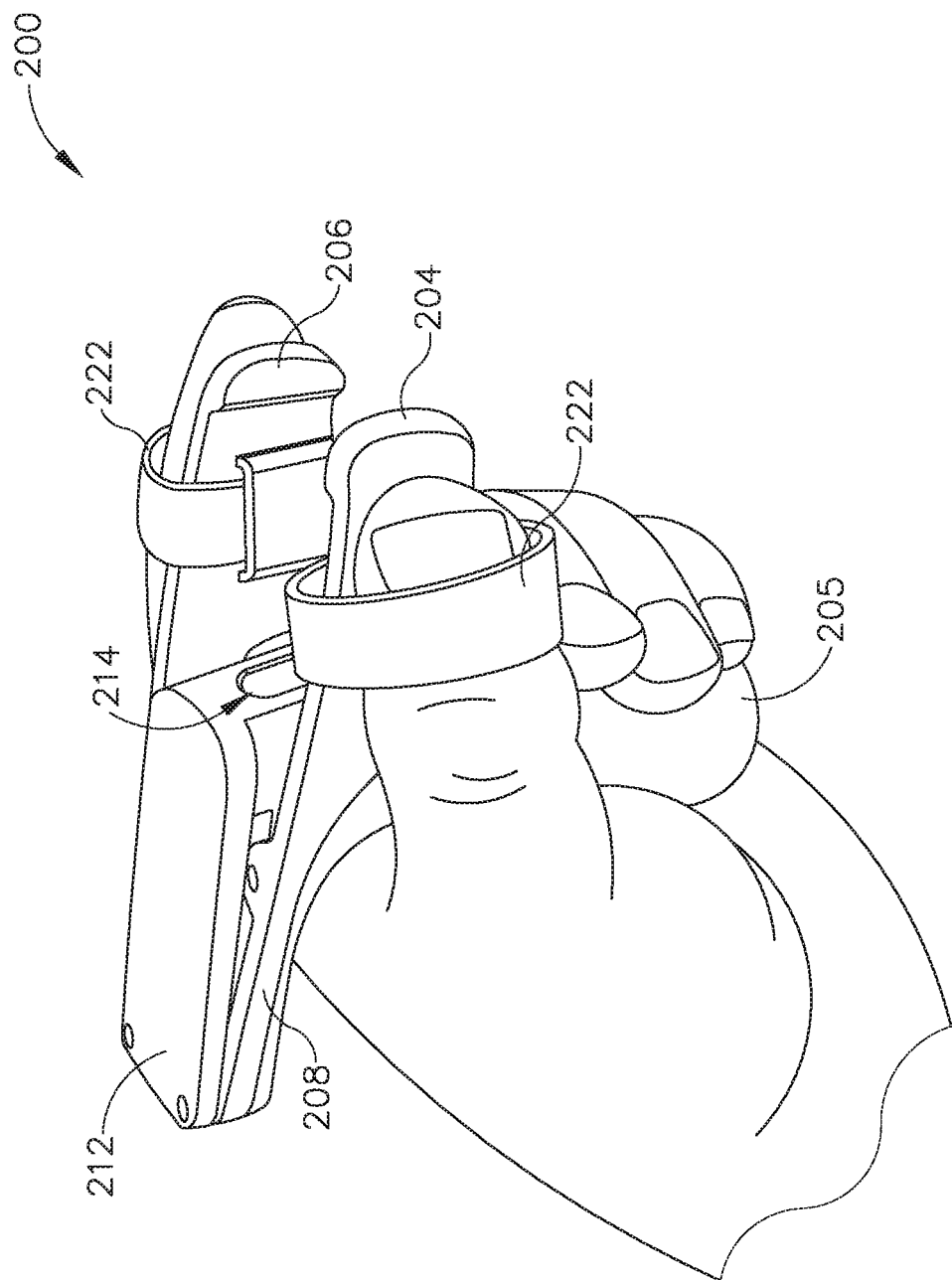
FIG. 11 depicts a perspective view of the user input device of FIG. 10A being grasped by an operator, where the set of pincher paddle buttons are in the open configuration and strapped to fingers of the operator.
Figure 12:
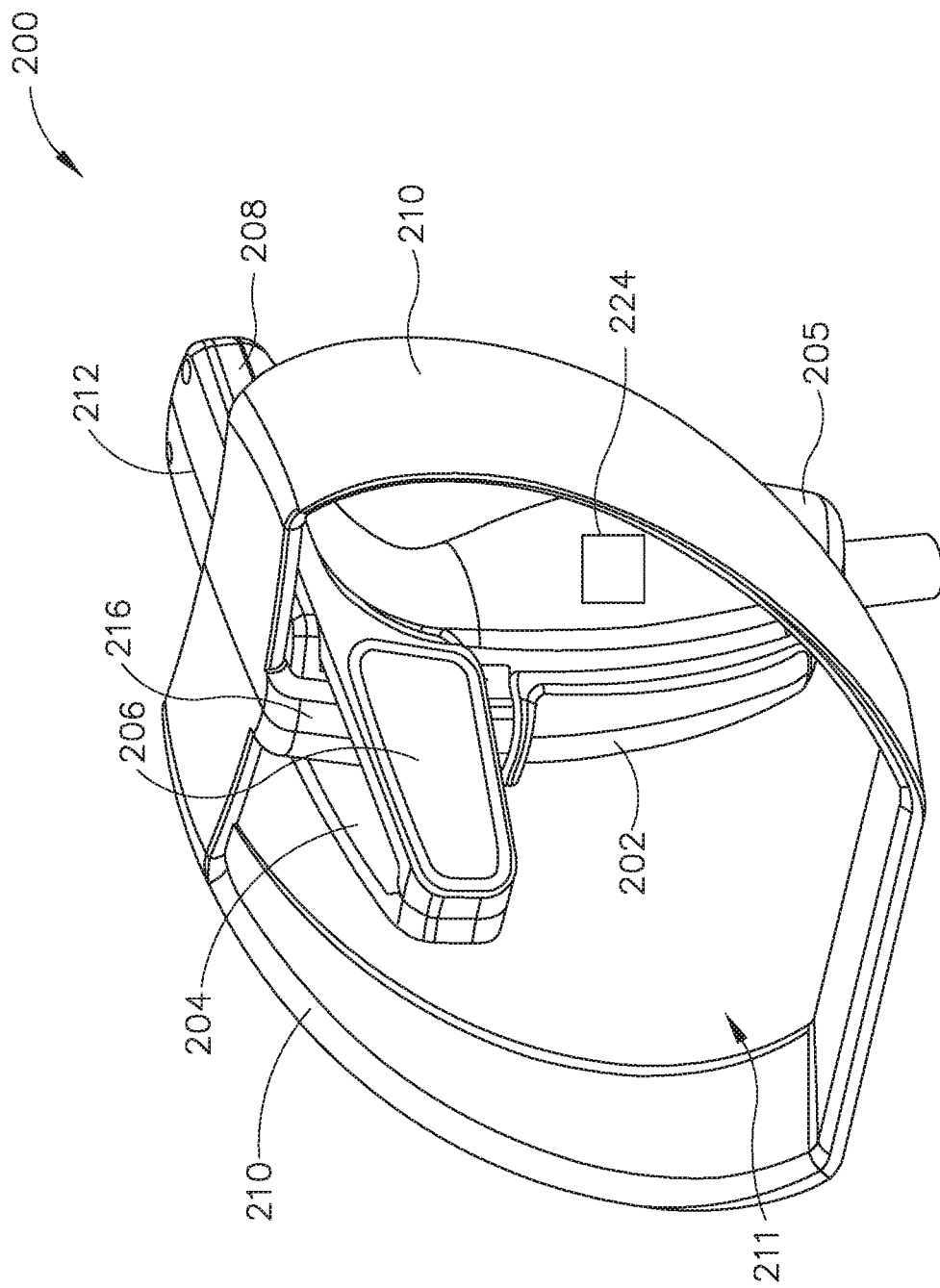
FIG. 12 depicts a perspective view of the user input device of FIG. 10A coupled with a position sensing ring.

User input device (200) also includes a pistol grip (205) connected to a distal body (212), a trigger (202), a pair of pincher paddle buttons (204, 206), a position sensor ring (210), and a pair of finger loops (222) attached to slots (220) of paddle buttons (204, 206). As best seen in FIG. 11, pistol grip (205) is dimensioned to be grasped by an operator with one hand such that the operator's thumb and index finger extend through finger loops (222) and contact the outside of pincher paddle buttons (204, 206), with the rest of the fingers of the same hand being adjacent to trigger (202). As will be described in greater detail below, trigger (202), pincher paddle buttons (204, 206), and position sensing ring (210) are all configured to generate control signals designed to control surgical instrument (150) and are all in communication with wireless communication device (224). Therefore, wireless communication device (224) may send control signals generated by pincher paddle buttons (204, 206), and position sensing ring (210) to processing device (26), which may then be communicated to robotic actuation assembly (48) as previously described above in order control surgical instrument (150).

Position sensing ring (210) includes a coupling member (216) and defines a hollow pathway (211). Coupling member (216) is configured to couple with complementary coupling member (214) of pistol grip (205) so that position sensor ring (210) is unitarily coupled with pistol grip (205). Hollow pathway (211) provides adequate room for an operator to grasp pistol grip (205) without contacting position sensing ring (210). Position sensing ring (210) may function substantially similar to position sensing assembly (110) described above. Therefore, position sensing ring (210) is configured to determine the axial location of user input device (200) along the X axis (X), Y axis (Y), and Z axis (Z); as well as the rotational position of user input device (200) about a longitudinal axis defined by distal body (212). In addition, or in the alternative, position sensing ring (210) may determine the rotational position of user input device about each of the X axis (X), Y axis (Y), and Z axis (Z). Position sensing ring (210) may thus provide position data relative to up to six dimensions. As pistol grip (205) and distal body (212) are translated along the X axis (X), Y axis (Y), and Z axis (Z); or rotated about the longitudinal axis defined by distal body (212), position sensing ring (210) generates a set of control signals corresponding to the axial translation and rotation.

Control signals may be sent to wireless communication device (224) through any suitable means as would be apparent to one having ordinary skill in the art in view of the teachings herein. Control signals corresponding to the translation and rotation of pistol grip (205) and distal body (212) along axes (X, Y, Z) and about the longitudinal axis defined by distal body (212) may then be communicated to robotic actuation assembly (48) via wireless communication devices (224, 28), first processing device (26), server (32), communication device (44), and second processing device (46) as described above. As best seen in FIG. 3 and FIG. 5, robotic actuation assembly (48) may receive corresponding control signals and then move the robotic arm attached to surgical instrument (150) so that surgical instrument (150) translates along axes (X, Y, Z) and rotates about longitudinal axis (LA2) to mimic movement of user input device (200). It should be understood that an operator may simultaneously view the corresponding movement of surgical instrument (150) via an endoscopic camera communicating live video images to viewing screen (25). Therefore, an operator may adjust the movement of user input device (200) based on visual feedback provided by robotic actuation assembly (48).

Position sensing ring (210) may determine the position of user input device (200) through any suitable means as would be apparent to one having ordinary skill in the art in view of the teachings herein, such as means described for position sensing assembly (110) above. For instance, position sensing ring (210) may include an internal coil that generates electrical current as user input device (200) is moved within an electromagnetic field, with the electrical current being indicative of movement and thus positioning of user input device (200) within a predefined space. Moreover, while position sensing ring (210) is used in the present example, it should be understood that any suitable combination of components and techniques may be used to provide position sensing, including but not limited to one or more accelerometers, optical sensing, electromagnetic field sensing, etc.

Figure 10A:
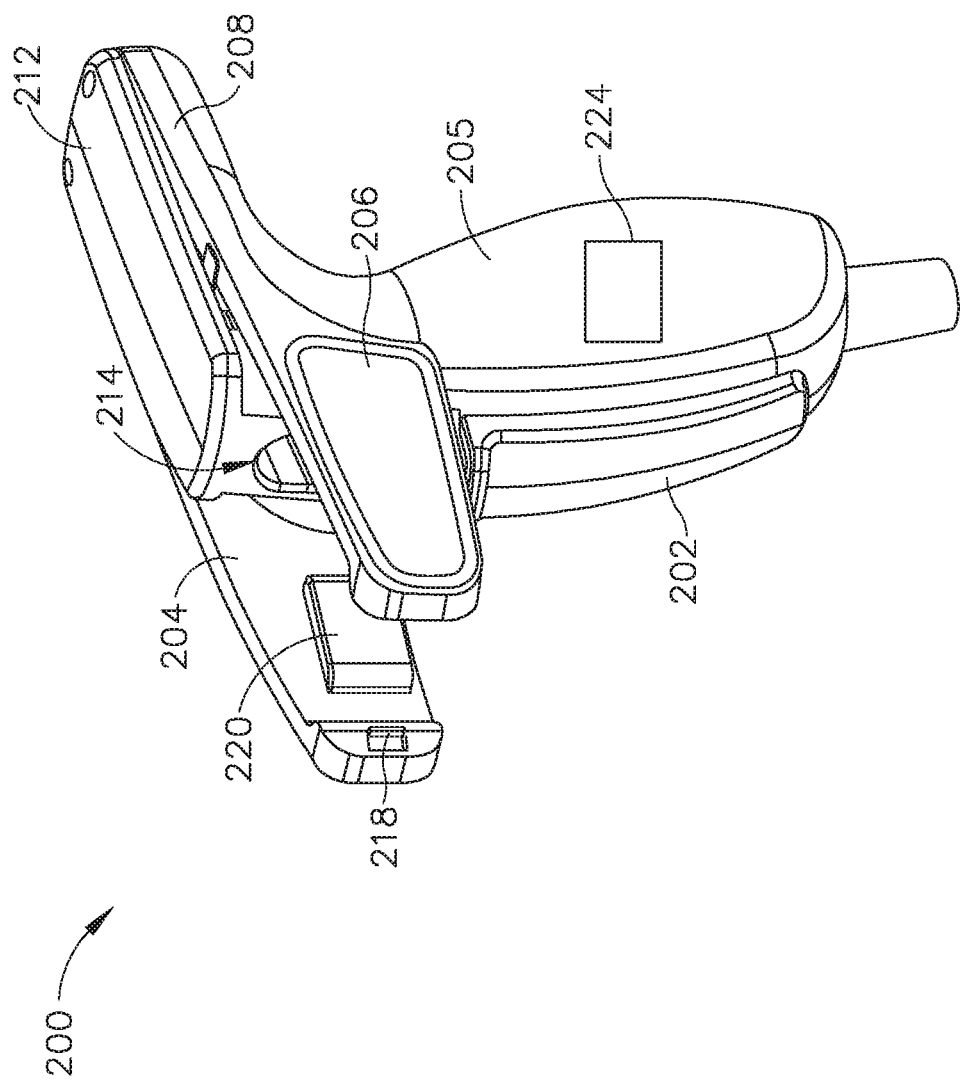
FIG. 10A depicts a perspective view of an alternative user input device that may be readily incorporated into the robotic surgical assembly of FIG. 1, where a set of pincher paddle buttons are in an open configuration.
Figure 10B:
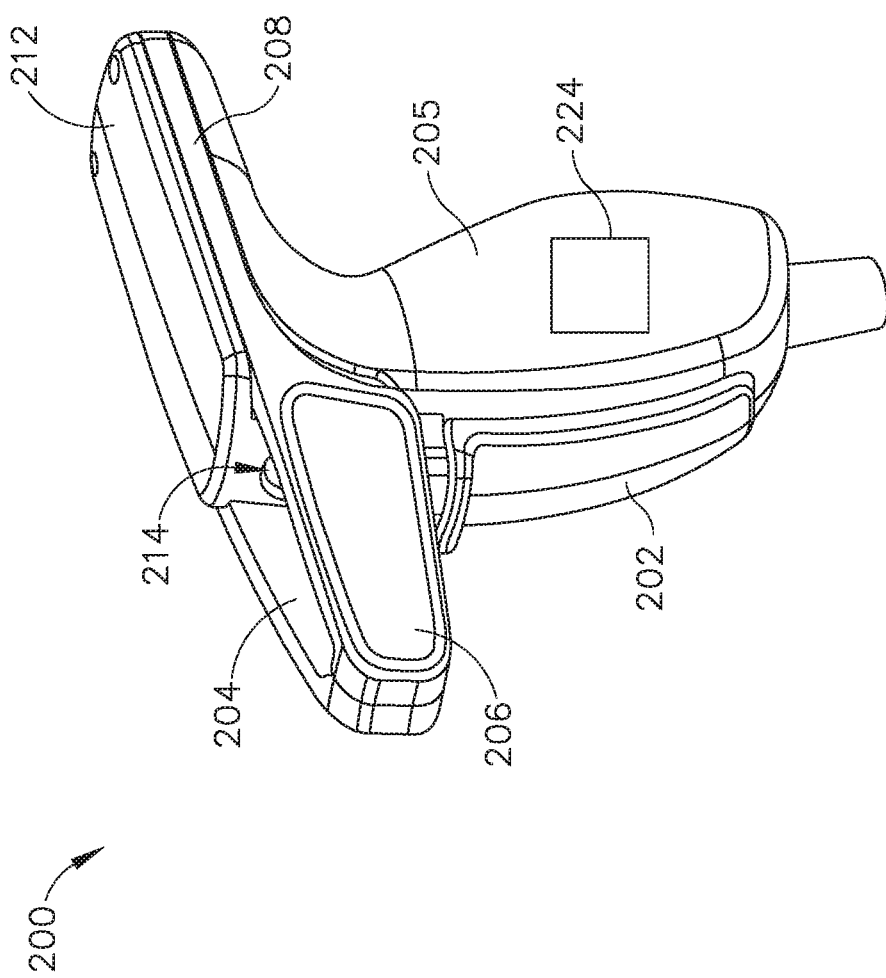
FIG. 10B depicts a perspective view of the user input device of FIG. 10A, where the set of pincher paddle buttons are in a closed configuration.

As mentioned above, and as will be described in greater detail below, trigger (202) and pincher paddle buttons (204, 206) are each configured to generate a control signal corresponding with a specific movement/actions of surgical instrument (150). Pincher paddle buttons (204, 206) each are connected to distal body (212) by resilient arms (208). Resilient arms (208) bias pincher paddle buttons (204, 206) to an open configuration as shown in FIG. 10A. Pincher paddle buttons (204, 206) are configured to close at the same rate from the open configuration shown in FIG. 10A to a closed configuration as shown in FIG. 10B.

Pincher paddle buttons (204, 206) include a pincher actuation sensor (218) that is configured to determine the distance between pincher paddle buttons (204, 206) as they transition from the open configuration to the closed configuration. Pincher actuation sensor (218) may determine the distance between pincher paddle buttons (204, 206) through any suitable means known in the art in view of the teachings herein. In some versions, pincher actuation sensor (218) generates a varying control signal based on the distance between paddle buttons (204, 206), which may in turn correspond to progressive closure or opening of jaw (156) or any other suitable function of surgical instrument (150) that would be apparent to one having ordinary skill in the art in view of the teachings herein. In some other versions, paddle buttons (204, 206) may generate a control signal that activates end effector (150) rather than close jaws (156, 158). Pincher actuation sensor (218) may also only be configured to generate a control signal when paddle buttons (204, 206) are in the closed configuration. In some versions, pincher actuation sensor (218) may also provide tactile/sound feedback to a user when pincher paddle buttons (204, 206) make contact with each other.

By way of example only, pincher actuation sensor (218) may include a magnet and a hall effect sensor or some other kind of proximity sensor arrangement. As another merely illustrative alternative, pincher actuation sensor (218) may include a reed switch or other kind of contact sensor. Thus, in some versions, pincher actuation sensor (218) is only sensitive to the diametric transition between the fully closed positon (FIG. 10B) and an at least partially open position, without being able to discern among partially open positions between the fully open position (FIG. 10A) and the fully closed position (FIG. 10B). Other suitable forms that pincher actuation sensor (218) may take will be apparent to those of ordinary skill in the art in view of the teachings herein. It should also be understood that, in some variations, pincher actuation sensor (218) may be located on or in resilient arms (208) and/or body (212).

Control signals may be sent to wireless communication device (224) via any suitable means as would be apparent to one having ordinary skill in the art in view of the teachings herein. Control signals corresponding to jaw (156) closure may then be communicated to robotic actuation assembly (48) via wireless communication devices (224, 28), first processing device (26), server (32), communication device (44), and second processing device (46) as described above. Robotic actuation assembly (48) may receive corresponding control signals and then close first jaw (156) toward second jaw (158). It should be understood that an operator may simultaneously view the corresponding movement of surgical instrument (150) via an endoscopic camera communicating live video images to viewing screen (25). Therefore, an operator may adjust the movement of user input device (200) based on visual feedback provided by robotic actuation assembly (48).

Trigger (202) being pulled toward pistol grip (205) generates a set of control signals corresponding end effector (154) activation, or any other suitable function that would be apparent to one having ordinary skill in the art in view of the teachings herein. Control signals may be sent to wireless communication device (224) via any suitable means as would be apparent to one having ordinary skill in the art in view of the teachings herein. Control signals corresponding to end effector (154) activation may then be communicated to robotic actuation assembly (48) via wireless communication devices (224, 28), first processing device (26), server (32), communication device (44), and second processing device (46) as described above. Robotic actuation assembly (48) may receive corresponding control signals and then activate end effector (150). It should be understood that an operator may simultaneously view the corresponding movement of surgical instrument (150) via an endoscopic camera communicating live video images to viewing screen (25). Therefore, an operator may adjust the movement of user input device (200) based on visual feedback provided by robotic actuation assembly (48).

C. Shears Grip User Input Device

Figure 13:
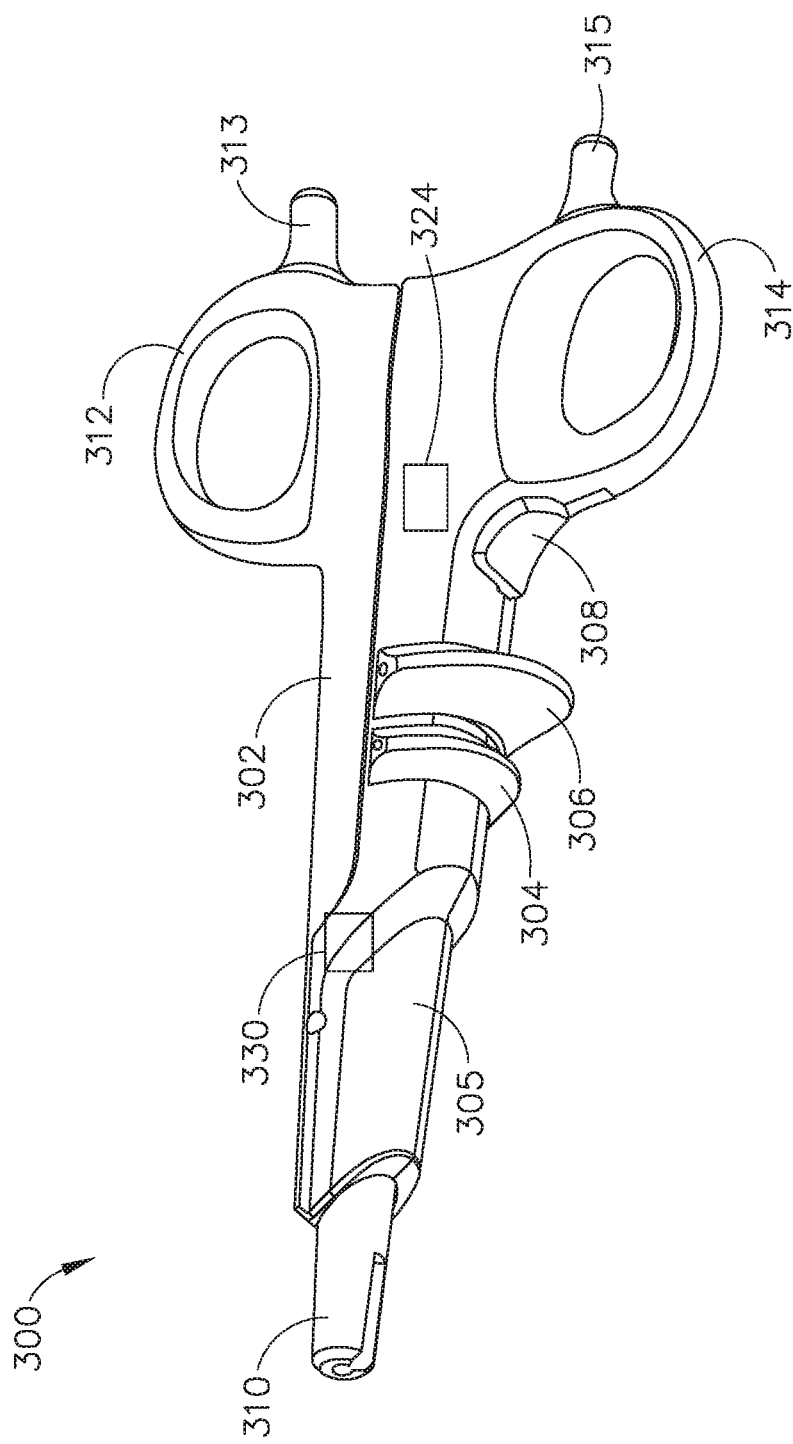
FIG. 13 depicts a perspective view of another alternative user input device that may be readily incorporated into robotic surgical assembly of FIG. 1.
Figure 14A:
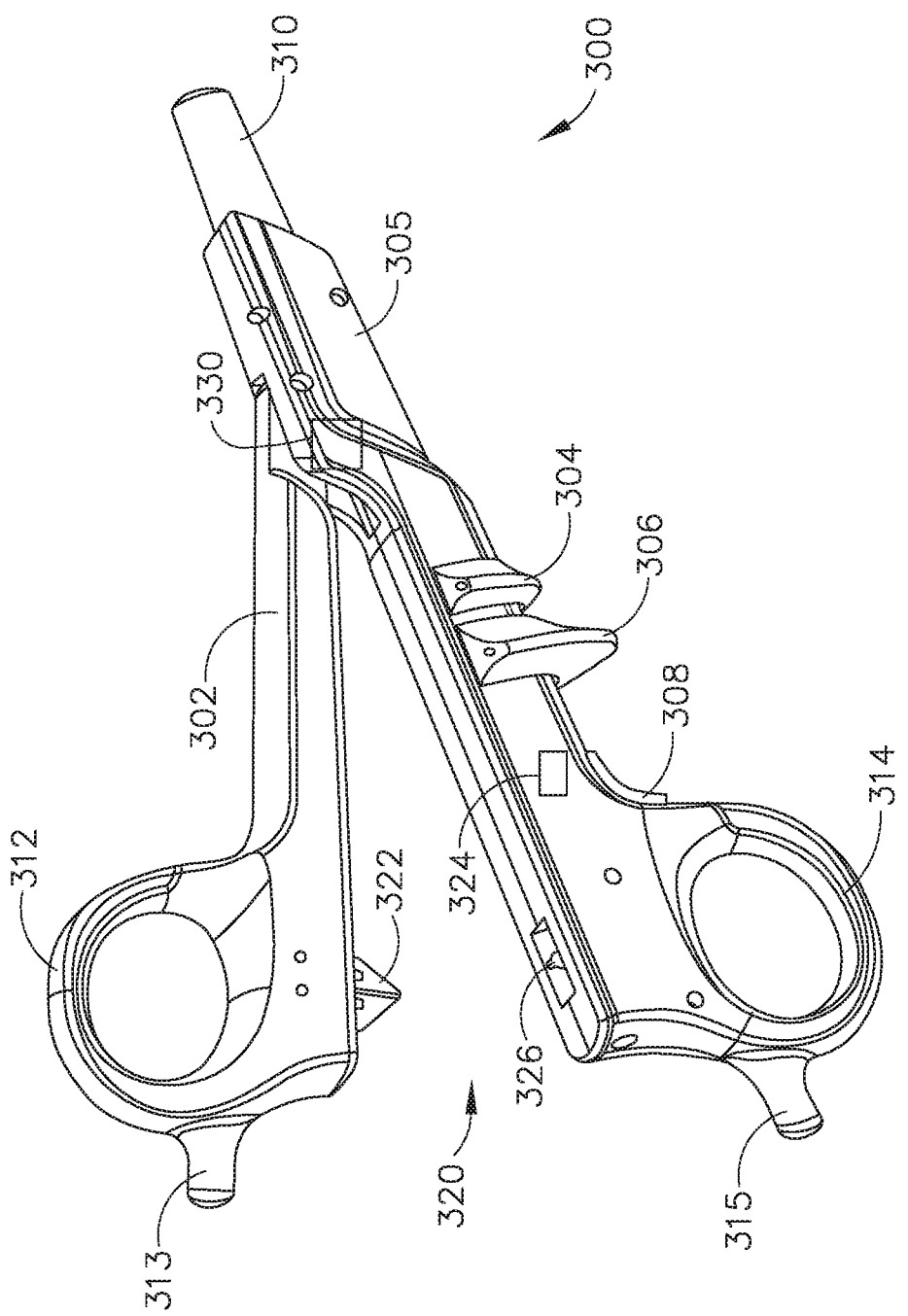
FIG. 14A depicts a perspective view of the user input device of FIG. 13 in an open configuration.
Figure 14B:
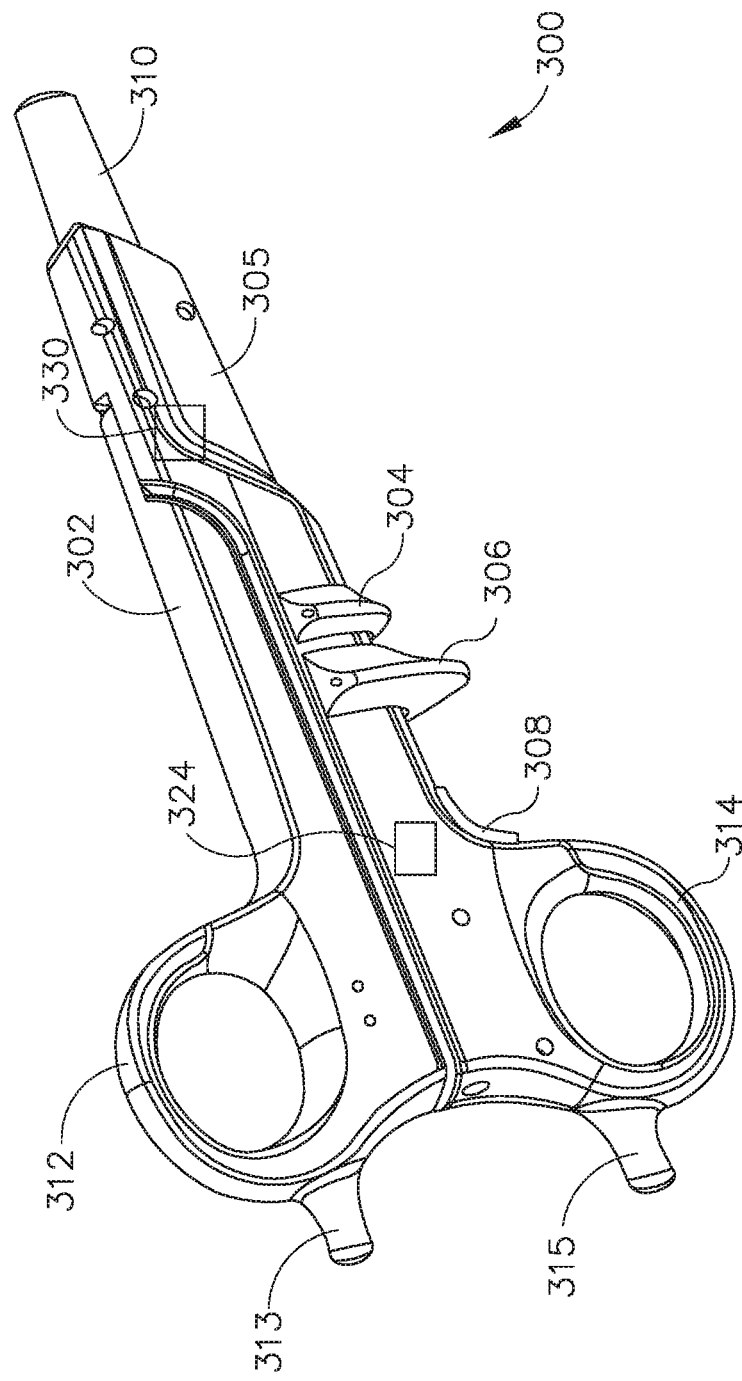
FIG. 14B depicts a perspective view of the user input device of FIG. 13 in a closed configuration.

FIGS. 13-14B show another exemplary alternative user input device (300) that may be readily incorporated into control assembly (20) of robotic surgical system (10) as a version of user input device assembly (22), in place of user input device (100, 200) described above. Therefore, user input device (300) may be used to control surgical instrument (150) or any other surgical instrument incorporated into a robotic arm of robotic actuation assembly (48).

User input device (300) of the present example is configured and operable just like user input device (100, 200) described above, with differences elaborated below. User input device (300) includes a wireless communication device (324), which is substantially similar to wireless communication device (24, 124, 224) described above. Therefore, user input device (300) may selectively communicate with processing device (26) by wireless communication device (324) selectively establishing communication with second wireless communication device (28). Additionally, as will be described in greater detail below, user input device (300) is configured to generate control signals that may be communicated to robotic actuation assembly (48) in order to move and/or activate surgical instrument (150).

User input device (300) also includes a body (305) defining a finger grip (314), a pivoting handle (302) defining a thumb grip (312), a rotational sensor (330), a position sensor assembly (310), buttons (304, 306, 308) associated with body (305), a hook (322) extending from pivoting handle (302), a latch (326) extending within body (305), and grip stability protrusions (313, 315) extending proximally from finger grip (314) and thumb grip (312). User input device (300) is dimensioned to be grasped similar to a set of surgical shears. Therefore, an operator may place their thumb within thumb grip (312) and a finger within finger grip (314) in order to grasp user input device (300). Protrusions (313, 315) are positioned and dimensioned to promote grip stability.

As best seen between FIGS. 14A-14B, an operator may pivot handle (302) toward and away body (305) between an open configuration (FIG. 14A) and a closed configuration (FIG. 14B). Hook (322) and latch (326) are configured to selectively lock pivoting handle (302) relative to body (305) while in the closed configuration.

Position sensing assembly (310) may function substantially similar to position sensing assembly (110) and position sensing ring (210) described above. Therefore, position sensing assembly (310) is configured to determine the axial location of user input device (300) along the X axis (X), Y axis (Y), and Z axis (Z); as well as the rotational position of user input device (300) about the longitudinal axis defined by body (305). In addition, or in the alternative, position sensing assembly (310) may determine the rotational position of user input device about each of the X axis (X), Y axis (Y), and Z axis (Z). Position sensing assembly (310) may thus provide position data relative to up to six dimensions. As body (305) is translated along the X axis (X), Y axis (Y), and Z axis (Z), or rotated about the longitudinal axis defined by body (305), position sensing assembly (310) generates a set of control signals corresponding to the axial translation and rotation.

Control signals may be sent to wireless communication device (324) through any suitable means as would be apparent to one having ordinary skill in the art in view of the teachings herein. Control signals corresponding to the translation and rotation of body (305) along axes (X, Y, Z) and about the longitudinal axis defined by body (305) may then be communicated to robotic actuation assembly (18) via wireless communication devices (324, 28), first processing device (26), server (32), communication device (44), and second processing device (46) as described above. As best seen in FIG. 3 and FIG. 5, robotic actuation assembly (48) may receive corresponding control signals and then move the robotic arm attached to surgical instrument (150) so that surgical instrument (150) translates along axes (X, Y, Z) and rotates about longitudinal axis (LA2) to mimic movement of user input device (300). It should be understood that an operator may simultaneously view the corresponding movement of surgical instrument (150) via an endoscopic camera communicating live video images to viewing screen (25). Therefore, an operator may adjust the movement of user input device (300) based on visual feedback provided by robotic actuation assembly (48).

Position sensing assembly (310) may determine the position of user input device (300) through any suitable means as would be apparent to one having ordinary skill in the art in view of the teachings herein, such as means described for position sensing assembly (110) above.

As mentioned above, and as will be described in greater detail below, pivoting handle (302) and buttons (304, 306, 308) are each configured to generate a control signal corresponding with a specific movement/actions of surgical instrument (150). Pivoting handle (302) may pivot relative to body (305) from the open configuration to the closed configuration. Rotational sensor (330) is located on either or both pivoting handle (302) of body (305) and is configured to determine the rotational position of pivoting handle (302) relative to body, and to generate a corresponding varying control signal which may in turn correspond to jaw (156) closure or any other suitable function of surgical instrument (150) that would be apparent to one having ordinary skill in the art in view of the teachings herein. For example, rotational sensor (330) may generate a control signal that activates end effector (150) rather than close jaws (156, 158). Rotational sensor (330) may also only be configured to generate a control signal when pivoting handle (302) is in the closed configuration. Rotational sensor (330) may determine the rotational position of pivoting handle (302) relative to body (305) through any suitable methods known by one having ordinary skill in the art in view of the teachings herein.

While rotational sensor (330) is described above as actuating a jaw (156) of a surgical stapler end effector (150), it should be understood that rotational sensor (330) may instead actuate a jaw of some other kind of end effector (150). By way of example only, in versions of robotic surgical system (10) where user input device (300) is used, end effector (150) may be in the form of an ultrasonic forceps end effector, having an ultrasonic blade and a pivoting clamp arm. In such versions, rotational sensor (330) may drive the clamp arm toward and away from the ultrasonic blade based on pivotal movement of handle (302) relative to body (305). Those of ordinary skill in the art will recognize that, since user input device (300) is configured similar to an ultrasonic shears instrument, this configuration may provide the operator with an intuitive, familiar "feel." In other words, when an operator who is experienced using conventional ultrasonic shears devices operates user input device (300) to control an ultrasonic shears version of end effector (150), the control of the ultrasonic shears version of end effector (150) may be more intuitive to the operator than the control might otherwise be if the operator were using a differently configured user input device (300).

Control signals may be sent to wireless communication device (324) via any suitable means as would be apparent to one having ordinary skill in the art in view of the teachings herein. Control signals corresponding to jaw (156) closure may then be communicated to robotic actuation assembly (48) via wireless communication devices (324, 28), first processing device (26), server (32), communication device (44), and second processing device (46) as described above. Robotic actuation assembly (48) may receive corresponding control signals and then close first jaw (156) toward second jaw (158). It should be understood that an operator may simultaneously view the corresponding movement of surgical instrument (150) via an endoscopic camera communicating live video images to viewing screen (25). Therefore, an operator may adjust the movement of user input device (300) based on visual feedback provided by robotic actuation assembly (48).

Buttons (304, 306, 308) being individually pulled each generate a set of control signals corresponding to end effector (154) activation, articulation, or any other suitable function that would be apparent to one having an ordinary skill in the art in view of the teachings herein. Additionally, while individual buttons (304, 306, 308) being pulled may have separate, unique functions, any combination of buttons (304, 306, 308) being pulled may also have unique functions. Control signals may be sent to wireless communication device (324) via any suitable means as would be apparent to one having ordinary skill in the art in view of the teachings herein. Control signals corresponding to end effector (154) activation may then be communicated to robotic actuation assembly (48) via wireless communication devices (324, 28), first processing device (26), server (32), communication device (44), and second processing device (46) as described above. Robotic actuation assembly (48) may receive corresponding control signals and then activate end effector (150). It should be understood that an operator may simultaneously view the corresponding movement of surgical instrument (150) via an endoscopic camera communicating live video images to viewing screen (25). Therefore, an operator may adjust the movement of user input device (300) based on visual feedback provided by robotic actuation assembly (48).

In versions where end effector (150) is in the form of an ultrasonic shears end effector, as noted above, buttons (304, 306) may be actuated to ultrasonically activate the ultrasonic blade of end effector (150). For instance, button (304) may activate the ultrasonic blade at one power level; and button (306) at another power level. In some variations where end effector (150) is in the form of an ultrasonic shears end effector that also has RF electrosurgical capabilities, button (308) may activate electrodes of end effector (150) to apply RF energy to tissue contacting end effector (150). Other suitable activations that may be provided in response to actuation of buttons (304, 306, 308) will be apparent to those of ordinary skill in the art in view of the teachings herein,

D. Stylus Style User Input Device

FIGS. 15A-17 show another exemplary alternative user input device (400) that may be readily incorporated into control assembly (20) of robotic surgical system (10) as a version of user input device assembly (22), in place of user input device (100, 200, 300) described above. Therefore, user input device (400) may be used to control surgical instrument (150) or any other surgical instrument incorporated into a robotic arm of robotic actuation assembly (48).

User input device (400) of the present example is configured and operable just like user input device (100, 200, 300) described above, with differences elaborated below. User input device (400) includes a wireless communication device (424), which is substantially similar to wireless communication device (24, 124, 224, 324) described above.

Therefore, user input device (400) may selectively communicate with processing device (26) by wireless communication device (424) selectively establishing communication with second wireless communication device (28). Additionally, as will be described in greater detail below, user input device (400) is configured to generate control signals that may be communicated to robotic actuation assembly (48) in order to move and/or activate surgical instrument (150).

User input device (400) also includes a body (405) defining an elongated stylus shape, a plurality of linkage buttons (402) circumferentially surrounding a portion of body (405), a sled (404) pivotally attached to the distal end of each linkage button (402), a tactile ring switch (406) located distal to sled (404), and a position sensor assembly (410). An operator may grip body (405) and linkage buttons (402) similar to that of a stylus, using a pencil grip or any other suitable grip.

Position sensing assembly (410) may function substantially similar to position sensing assembly (110, 310) and position sensing ring (210) described above. Therefore, position sensing assembly (410) is configured to determine the axial location of user input device (400) along the X axis (X), Y axis (Y), and Z axis (Z); as well as the rotational position of user input device (400) about the longitudinal axis defined by body (405). In addition, or in the alternative, position sensing assembly (410) may determine the rotational position of user input device about each of the X axis (X), Y axis (Y), and Z axis (Z). Position sensing assembly (410) may thus provide position data relative to up to six dimensions. As body (405) is translated along the X axis (X), Y axis (Y), and Z axis (Z); or rotated about the longitudinal axis defined by body (405), position sensing assembly (310) generates a set of control signals corresponding to the axial translation and rotation.

Control signals may be sent to wireless communication device (424) through any suitable means as would be apparent to one having ordinary skill in the art in view of the teachings herein. Control signals corresponding to the translation and rotation of body (405) along axes (X, Y, Z) and about the longitudinal axis defined by body (405) may then be communicated to robotic actuation assembly (48) via wireless communication devices (424, 28), first processing device (26), server (32), communication device (44), and second processing device (46) as described above. As best seen in FIG. 3 and FIG. 5, robotic actuation assembly (48) may receive corresponding control signals and then move the robotic arm attached to surgical instrument (150) so that surgical instrument (150) translates along axes (X, Y, Z) and rotates about longitudinal axis (LA2) to mimic movement of user input device (300). It should be understood that an operator may simultaneously view the corresponding movement of surgical instrument (150) via an endoscopic camera communicating live video images to viewing screen (25). Therefore, an operator may adjust the movement of user input device (400) based on visual feedback provided by robotic actuation assembly (48).

Position sensing assembly (410) may determine the position of user input device (400) through any suitable means as would be apparent to one having ordinary skill in the art in view of the teachings herein, such as means described for position sensing assembly (110) above.

Figure 15A:
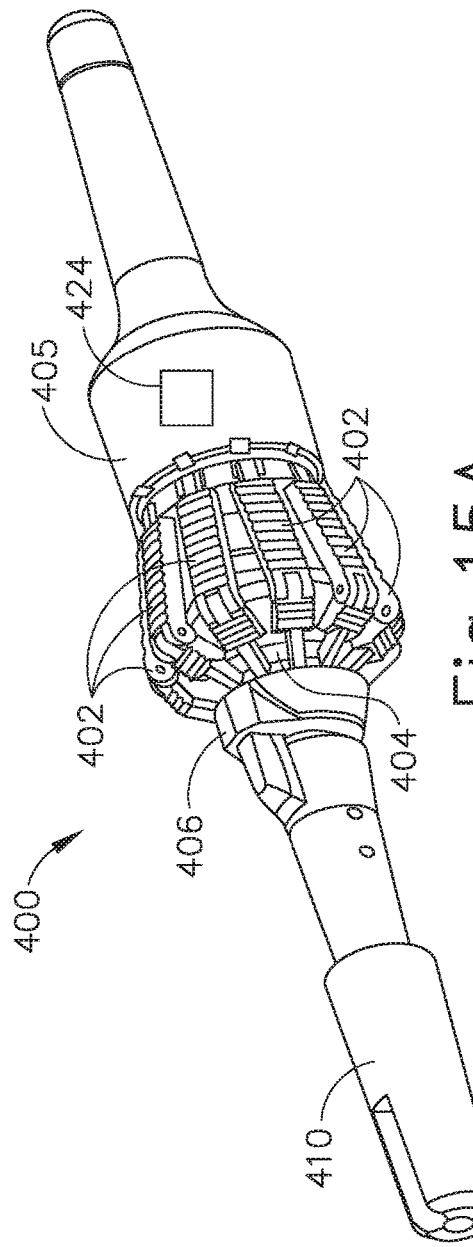
FIG. 15A depicts a perspective view of another exemplary user input device that may be readily incorporated into the robotic surgical assembly of FIG. 1, where the activation buttons are in an open configuration.
Figure 15B:
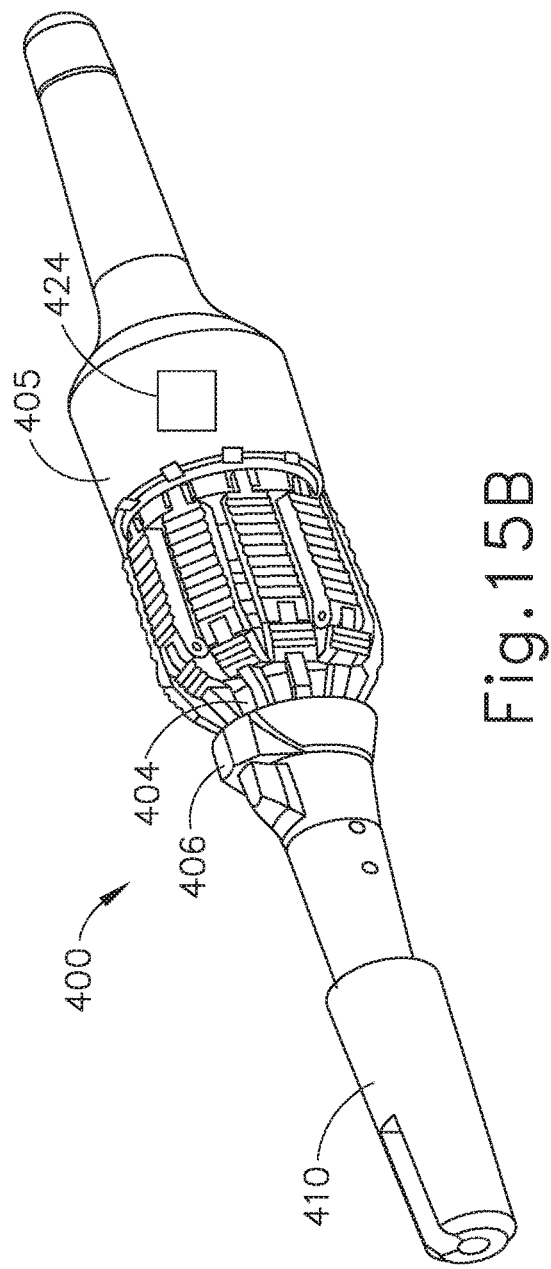
FIG. 15B depicts a perspective view of the user input device of FIG. 15A, where the activation buttons are in a closed configuration.

As shown between FIGS. 15A-15B, linkage buttons (402) may unitarily actuate from an open configuration (FIG. 15A.) to a closed configuration (15B). The proximal ends of linkage buttons (402) are pivotally connected to body (405). The distal ends of linkage buttons (402) are pivotally connected to sled (404). Linkage buttons (402) are each in the form of two segments that are pivotally coupled with each other, such that linkage buttons (402) are operable to transition between a collapsed state (FIG. 15A) and an elongated state (FIG. 15B). Sled (404) is also in communication with wireless communication device (324). Therefore, sled (404) may longitudinally translate along body (405) in response to linkage buttons (402) moving from the open configuration to the closed configuration.

Sled (404) is configured to generate a varying control signal based on the longitudinal location of sled (404) along body (405), which may in turn correspond to jaw (156) closure or any other suitable function of surgical instrument (150) that would be apparent to one having ordinary skill in the art in view of the teachings herein. When sled (404) is actuated to the position shown in FIG. 15B, sled (404) makes contact with tactile ring switch (406), which then generates a separate, second, control signal, which may in turn correspond to activating end effector (154) or any other suitable function of surgical instrument (150) that would be apparent to one having ordinary skill in the art in view of the teachings herein. Tactile ring switch (406) may provide a tactile response when activated. Additional force may be needed to activate tactile ring switch (406) as compared to just translating sled (404) relative to body (405). Tactile ring switch (406) is also in communication with wireless communication device (324).

Varying control signals generated by the longitudinal position of sled (404) relative to body (405) and the second control signal generated by tactile ring switch (406) may be sent to wireless communication device (424) via any suitable means as would be apparent to one having ordinary skill in the art in view of the teachings herein. Control signals corresponding to jaw (156) closure and activation of end effector (154) may then be communicated to robotic actuation assembly (48) via wireless communication devices (424, 28), first processing device (26), server (32), communication device (44), and second processing device (46) as described above. Once robotic actuation assembly (48) receives the varying control signal from sled (404), robotic actuation assembly (48) may then close first jaw (156) toward second jaw (158). One robotic actuation assembly (48) receives the second control signal from tactile ring switch (406), end effector (154) may be activated. It should be understood that an operator may simultaneously view the corresponding movement of surgical instrument (150) via an endoscopic camera communicating live video images to viewing screen (25). Therefore, an operator may adjust the movement of user input device (400) based on visual feedback provided by robotic actuation assembly (48).

While user input device (400) is described above as being used to operate a surgical stapler end effector (150), it should be understood that user input device (400) may instead operate some other kind of end effector (150). By way of example only, in versions of robotic surgical system (10) where user input device (400) is used, end effector (150) may be in the form of an ultrasonic scalpel end effector, having an ultrasonic blade. In such versions, tactile ring switch (406) may selectively activate the ultrasonic blade based on linkage buttons (402) reaching the closed configuration. Those of ordinary skill in the art will recognize that, to the extent that user input device (400) is configured similar to an ultrasonic scalpel instrument, this configuration may provide the operator with an intuitive, familiar "feel." In other words, when an operator who is experienced using conventional ultrasonic scalpel devices operates user input device (400) to control an ultrasonic scalpel version of end effector (150), the control of the ultrasonic scalpel version of end effector (150) may be more intuitive to the operator than the control might otherwise be if the operator were using a differently configured user input device (400).

E. Forceps Grip Style User Input Device

Figure 18:
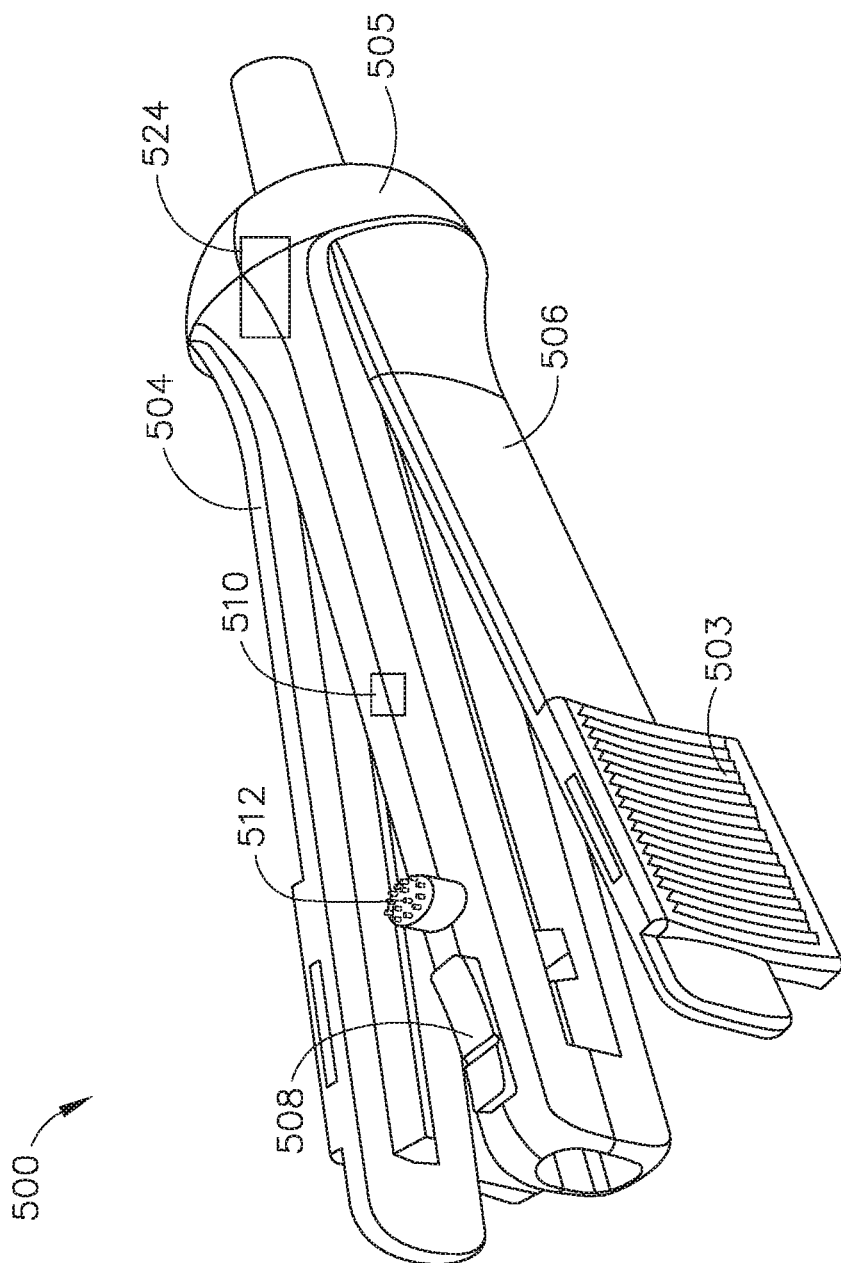
FIG. 18 depicts a perspective view of another exemplary user input device that may be readily incorporated into the robotic surgical assembly of FIG. 1, where the moving actuators are in an open configuration.

FIGS. 18-19B show another exemplary alternative user input device (500) that may be readily incorporated into control assembly (20) of robotic surgical system (10) as a version of user input device assembly (22), in place of user input device (100, 200, 300, 400) described above. Therefore, user input device (500) may be used to control surgical instrument (150) or any other surgical instrument incorporated into a robotic arm of robotic actuation assembly (48).

User input device (500) of the present example is configured and operable just like user input device (100, 200, 300, 400) described above, with differences elaborated below. User input device (500) includes a wireless communication device (524), which is substantially similar to wireless communication device (24, 124, 224, 324, 424) described above. Therefore, user input device (500) may selectively communicate with processing device (26) by wireless communication device (524) selectively establishing communication with second wireless communication device (28). Additionally, as will be described in greater detail below, user input device (500) is configured to generate control signals that may be communicated to robotic actuation assembly (48) in order to move and/or activate surgical instrument (150).

User input device (500) also includes a body (505), a pair of actuators (504, 506) pivotally connected to a proximal end of body (505), a position sensor assembly (510), a toggle button (508), and a button (512). An operator may grasp actuators (504, 506) with grips (503) between a thumb and fingers to hold user input device (500) like a pair of forceps. Actuators (504, 506) are biased to an open configuration as shown in FIGS. 18 and 19A. Actuators (504, 506) may pivot at the same rate relative to body (505) from the open configuration to a closed configuration as shown between FIGS. 19A-19B.

Position sensing assembly (510) may function substantially similar to position sensing assembly (110, 210, 310, 410) and position sensing ring (210) described above. Therefore, position sensing assembly (510) is configured to determine the axial location of user input device (500) along the X axis (X), Y axis (Y), and Z axis (Z); as well as the rotational position of user input device (500) about the longitudinal axis defined by body (505). In addition, or in the alternative, position sensing assembly (510) may determine the rotational position of user input device about each of the X axis (X), Y axis (Y), and Z axis (Z). Position sensing assembly (510) may thus provide position data relative to up to six dimensions. As body (505) is translated along the X axis (X), Y axis (Y), and Z axis (Z); or rotated about the longitudinal axis defined by body (505), position sensing assembly (510) generates a set of control signals corresponding to the axial translation and rotation.

Control signals may be sent to wireless communication device (524) through any suitable means as would be apparent to one having ordinary skill in the art in view of the teachings herein. Control signals corresponding to the translation and rotation of body (505) along axes (X, Y, Z) and about the longitudinal axis defined by body (505) may then be communicated to robotic actuation assembly (48) via wireless communication devices (524, 28), first processing device (26), server (32), communication device (44), and second processing device (46) as described above. As best seen in FIG. 3 and FIG. 5, robotic actuation assembly (48) may receive corresponding control signals and then move the robotic arm attached to surgical instrument (150) so that surgical instrument (150) translates along axes (X, Y, Z) and rotates about longitudinal axis (LA2) to mimic movement of user input device (500). It should be understood that an operator may simultaneously view the corresponding movement of surgical instrument (150) via an endoscopic camera communicating live video images to viewing screen (25). Therefore, an operator may adjust the movement of user input device (500) based on visual feedback provided by robotic actuation assembly (48).

Position sensing assembly (510) may determine the position of user input device (500) through any suitable means as would be apparent to one having ordinary skill in the art in view of the teachings herein, such as means described for position sensing assembly (110) above.

Actuators (504, 506) are configured to determine the rotational displacement of actuators (504, 506) relative to body (505) as they transition from the open configuration to the closed configuration. Actuators (504, 506) may determine the rotational displacement through any suitable means known in the art in view of the teachings herein. In some versions, actuators (504, 506) generate a varying control signal based on the distance between actuators (504, 506) and body (505), which may in turn correspond to progressive closure or opening of jaw (156) or any other suitable function of surgical instrument (150) that would be apparent to one having ordinary skill in the art in view of the teachings herein. In some other versions, actuators (504, 506) may generate a control signal that activates end effector (150) rather than close jaws (156, 158). Actuators (504, 506) may also be configured to only generate a control signal when actuators (504, 506) are in the closed configuration. In some versions, actuators (504, 506) may also provide tactile/sound feedback to a user when actuators (504, 506) make contact with body (505) in the closed position.

Control signals may be sent to wireless communication device (524) via any suitable means as would be apparent to one having ordinary skill in the art in view of the teachings herein. Control signals corresponding to jaw (156) closure may then be communicated to robotic actuation assembly (48) via wireless communication devices (524, 28), first processing device (26), server (32), communication device (44), and second processing device (46) as described above. Robotic actuation assembly (48) may receive corresponding control signals and then close first jaw (156) toward second jaw (158). It should be understood that an operator may simultaneously view the corresponding movement of surgical instrument (150) via an endoscopic camera communicating live video images to viewing screen (25). Therefore, an operator may adjust the movement of user input device (500) based on visual feedback provided by robotic actuation assembly (48).

Buttons (508, 512) being individually activated each generate a set of control signals corresponding to end effector (154) activation, articulation, or any other suitable function that would be apparent to one having an ordinary skill in the art in view of the teachings herein. Toggle button (508) may have two functions depending on the direction toggle button (508) in which is actuated. Additionally, while individual buttons (508, 512) being actuated may have separate, unique functions, any combination of buttons (508, 512) being actuated may also have unique functions. Control signals may be sent to wireless communication device (524) via any suitable means as would be apparent to one having ordinary skill in the art in view of the teachings herein.

Control signals corresponding to end effector (154) activation or articulation may then be communicated to robotic actuation assembly (48) via wireless communication devices (524, 28), first processing device (26), server (32), communication device (44), and second processing device (46) as described above. Robotic actuation assembly (48) may receive corresponding control signals and then activate or articulate end effector (150). It should be understood that an operator may simultaneously view the corresponding movement of surgical instrument (150) via an endoscopic camera communicating live video images to viewing screen (25). Therefore, an operator may adjust the movement of user input device (500) based on visual feedback provided by robotic actuation assembly (48).

F. Pistol Grip User Input Device with Laparoscopic Tool Style Controls

Figure 20:
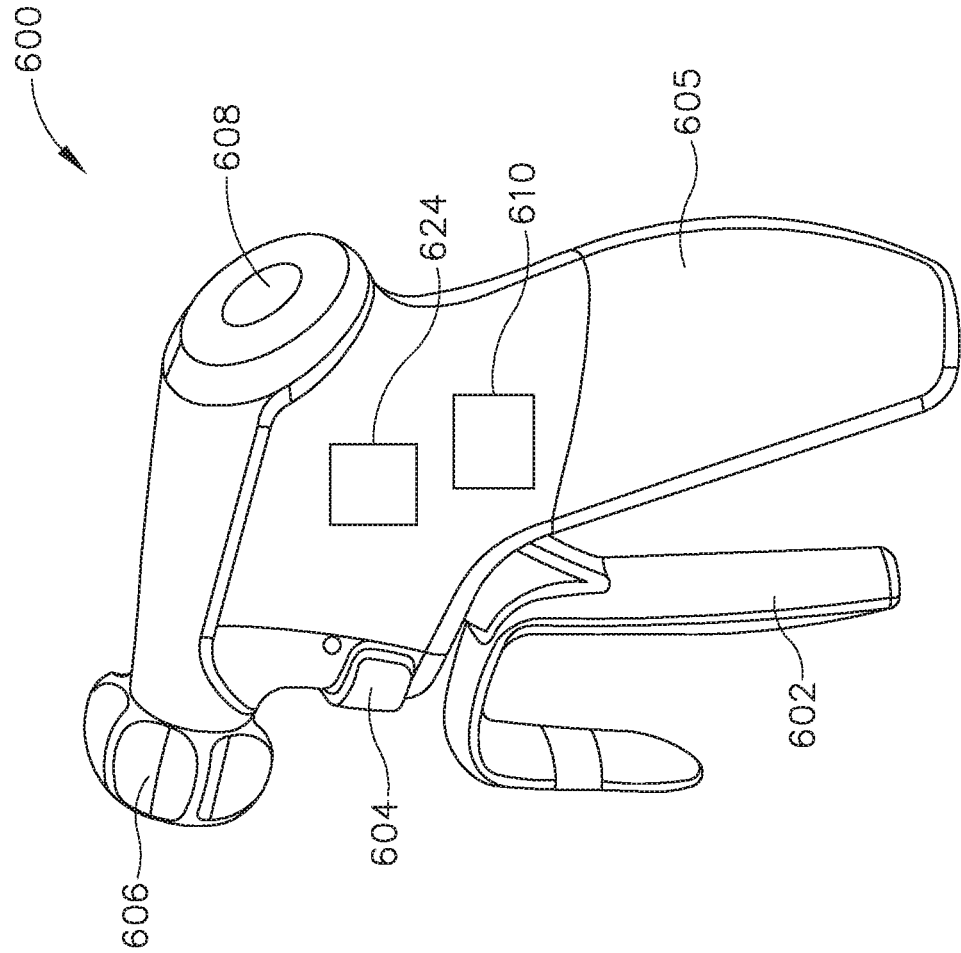
FIG. 20 depicts a perspective view of another exemplary user input device that may be readily incorporated into the robotic surgical assembly of FIG. 1.
Figure 21:
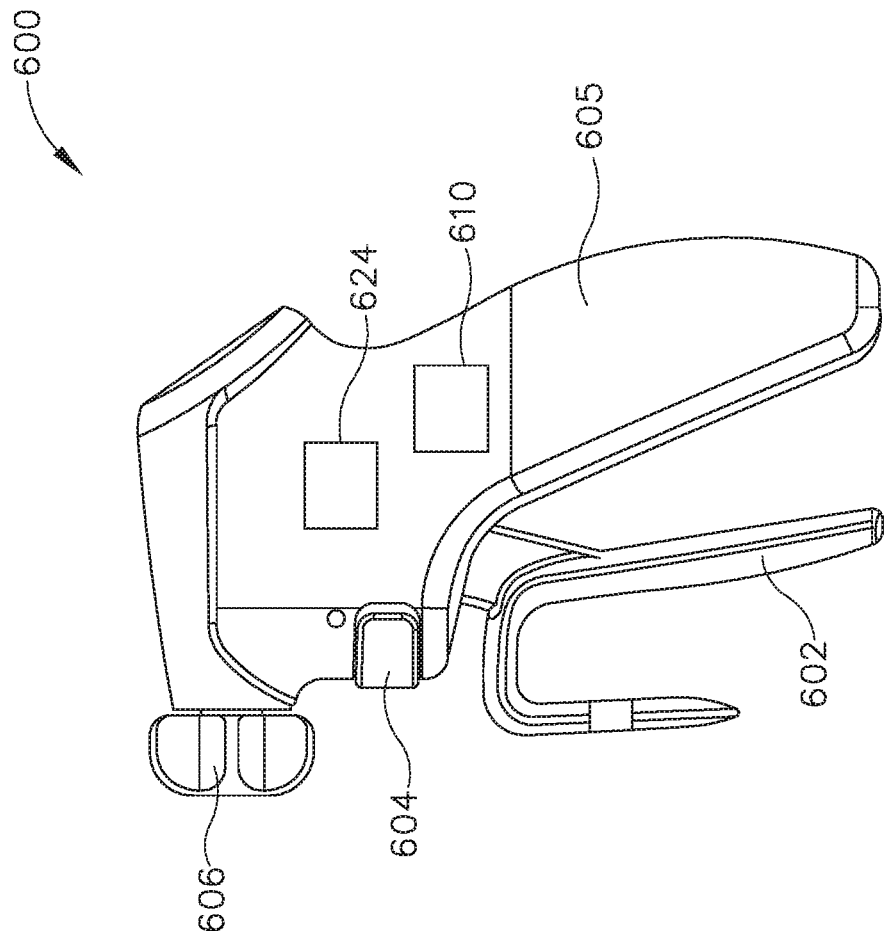
FIG. 21 depicts an elevational side view of the user input device of FIG. 20.
Figure 22:
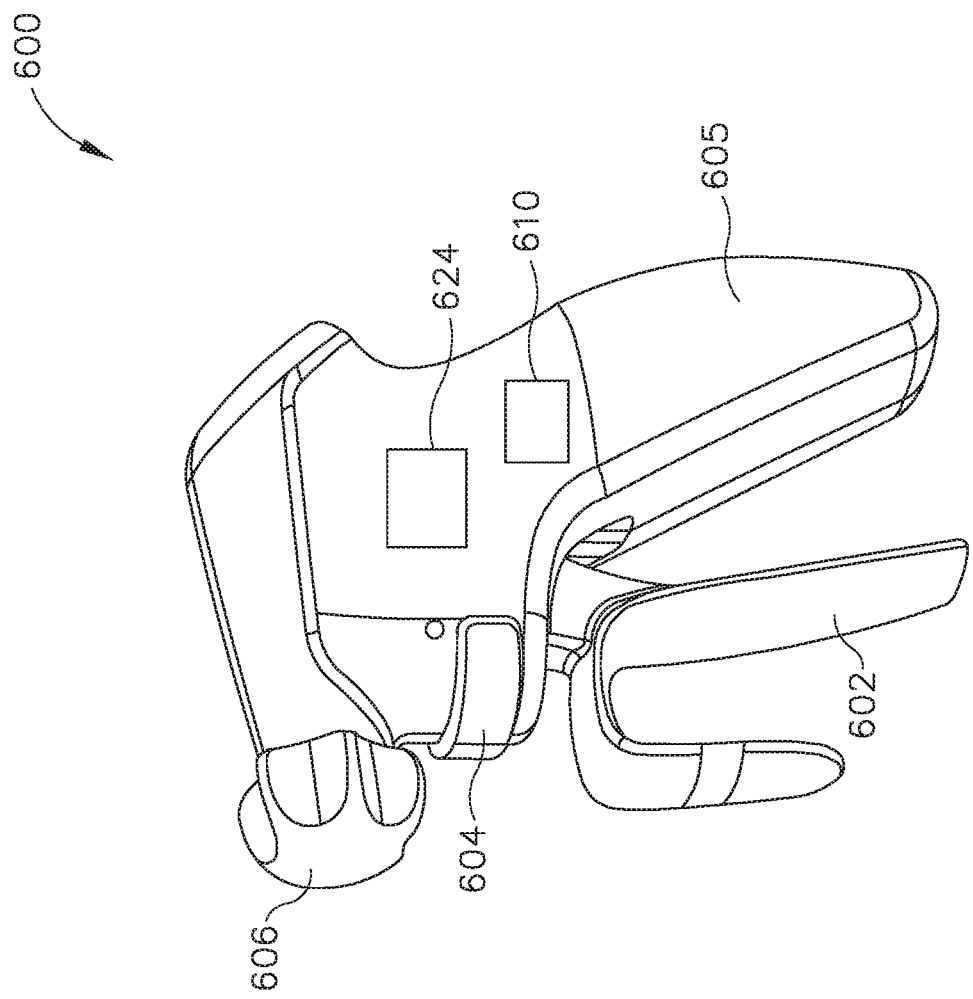
FIG. 22 depicts another perspective view of the user input device of FIG. 20.

FIGS. 20-22 show another exemplary alternative user input device (600) that may be readily incorporated into control assembly (20) of robotic surgical system (10) as a version of user input device assembly (22), in place of user input device (100, 200, 300, 400, 500) described above. Therefore, user input device (600) may be used to control surgical instrument (150) or any other surgical instrument incorporated into a robotic arm of robotic actuation assembly (48).

User input device (600) of the present example is configured and operable just like user input device (100, 200, 300, 400, 500) described above, with differences elaborated below. User input device (600) includes a wireless communication device (624), which is substantially similar to wireless communication device (24, 124, 224, 324, 424, 524) described above. Therefore, user input device (600) may selectively communicate with processing device (26) by wireless communication device (624) selectively establishing communication with second wireless communication device (28). Additionally, as will be described in greater detail below, user input device (600) is configured to generate control signals that may be communicated to robotic actuation assembly (48) in order to move and/or activate surgical instrument (150).

User input assembly (600) also includes a pistol grip body (605), a pivoting trigger (602), a button (604), a rotation knob (606), a capacitive touch control area (608), and a position sensor assembly (610). Pistol grip body (605) may be grasped by one hand of an operator such that an operator may pivot trigger (602) toward pistol grip body (605) and activate button (604) with the same hand grasping pistol grip body (605). Trigger (602) may be biased to an open configuration. An operator may also rotate knob (606) with another hand in order to generate another control signal or to toggle through potential settings. Capacitive touch control area (608) may be activated by the thumb of the hand grasping pistol grip body (605), to select from various instrument functions and/or provide some other form of activation at end effector (150).

Position sensing assembly (610) may function substantially similar to position sensing assembly (110, 210, 310, 410, 510) and position sensing ring (210) described above. Therefore, position sensing assembly (610) is configured to determine the axial location of user input device (600) along the X axis (X), Y axis (Y), and Z axis (Z); as well as the rotational position of user input device (600) about the longitudinal axis defined by body (605). In addition, or in the alternative, position sensing assembly (610) may determine the rotational position of user input device about each of the X axis (X), Y axis (Y), and Z axis (Z). Position sensing assembly (610) may thus provide position data relative to up to six dimensions. As body (605) is translated along the X axis (X), Y axis (Y), and Z axis (Z), or rotated about the longitudinal axis defined by body (605), position sensing assembly (610) generates a set of control signals corresponding to the axial translation and rotation. It should be understood that position sensing assembly (610) of the current example may not have to generate control signals based on rotational location of user input device (600), as rotation knob (606) may control this feature.

Control signals may be sent to wireless communication device (624) through any suitable means as would be apparent to one having ordinary skill in the art in view of the teachings herein. Control signals corresponding to the translation and rotation of body (605) along axes (X, Y, Z) and about the longitudinal axis defined by body (605) may then be communicated to robotic actuation assembly (48) via wireless communication devices (624, 28), first processing device (26), server (32), communication device (44), and second processing device (46) as described above. As best seen in FIG. 3 and FIG. 5, robotic actuation assembly (48) may receive corresponding control signals and then move the robotic arm attached to surgical instrument (150) so that surgical instrument (150) translates along axes (X, Y, Z) and rotates about longitudinal axis (LA2) to mimic movement of user input device (600). It should be understood that an operator may simultaneously view the corresponding movement of surgical instrument (150) via an endoscopic camera communicating live video images to viewing screen (25). Therefore, an operator may adjust the movement of user input device (600) based on visual feedback provided by robotic actuation assembly (48).

Position sensing assembly (610) may determine the position of user input device (500) through any suitable means as would be apparent to one having ordinary skill in the art in view of the teachings herein, such as means described for position sensing assembly (110) above.

Trigger (602) may be pulled toward body (605) to generate a set of control signals corresponding to jaw (156) closure or any other suitable function that would be apparent to one having ordinary skill in the art in view of the teachings herein. Control signals may be sent to wireless communication device (624) via any suitable means as would be apparent to one having ordinary skill in the art in view of the teachings herein. Control signals corresponding to jaw (156) closure may then be communicated to robotic actuation assembly (48) via wireless communication devices (624, 28), first processing device (26), server (32), communication device (44), and second processing device (46) as described above. Robotic actuation assembly (48) may receive corresponding control signals and then close first jaw (156) toward second jaw (158). It should be understood that an operator may simultaneously view the corresponding movement of surgical instrument (150) via an endoscopic camera communicating live video images to viewing screen (25). Therefore, an operator may adjust the movement of user input device (600) based on visual feedback provided by robotic actuation assembly (48).

Button (604) being activated may generate a set of control signals corresponding to end effector (154) activation, articulation, or any other suitable function that would be apparent to one having an ordinary skill in the art in view of the teachings herein. Control signals may be sent to wireless communication device (624) via any suitable means as would be apparent to one having ordinary skill in the art in view of the teachings herein. Control signals corresponding to end effector (154) activation may then be communicated to robotic actuation assembly (48) via wireless communication devices (624, 28), first processing device (26), server (32), communication device (44), and second processing device (46) as described above. Robotic actuation assembly (48) may receive corresponding control signals and then activate end effector (150). It should be understood that an operator may simultaneously view the corresponding movement of surgical instrument (150) via an endoscopic camera communicating live video images to viewing screen (25). Therefore, an operator may adjust the movement of user input device (600) based on visual feedback provided by robotic actuation assembly (48).

Rotation of knob (606) may generate a set of control signals corresponding to rotating shaft assembly (152) about its own longitudinal axis (LA2), or any other suitable function that would be apparent to one having an ordinary skill in the art in view of the teachings herein. Control signals may be sent to wireless communication device (624) via any suitable means as would be apparent to one having ordinary skill in the art in view of the teachings herein. Control signals corresponding to rotation of shaft assembly (152) may then be communicated to robotic actuation assembly (48) via wireless communication devices (624, 28), first processing device (26), server (32), communication device (44), and second processing device (46) as described above. Robotic actuation assembly (48) may receive corresponding control signals and then rotate shaft assembly (152). It should be understood that an operator may simultaneously view the corresponding movement of surgical instrument (150) via an endoscopic camera communicating live video images to viewing screen (25). Therefore, an operator may adjust the movement of user input device (600) based on visual feedback provided by robotic actuation assembly (48).

While user input device (600) is described above as being used to operate a surgical stapler end effector (150), it should be understood that user input device (600) may instead operate some other kind of end effector (150). By way of example only, in versions of robotic surgical system (10) where user input device (600) is used, end effector (150) may be in the form of an ultrasonic forceps end effector, having an ultrasonic blade and a pivoting clamp arm. In such versions, trigger (602) may selectively actuate the clamp arm toward and away from the ultrasonic blade. In addition, button (604) may selectively activate the ultrasonic blade. Those of ordinary skill in the art will recognize that, to the extent that user input device (600) is configured similar to a handle assembly of an ultrasonic forceps instrument, this configuration may provide the operator with an intuitive, familiar "feel." In other words, when an operator who is experienced using conventional ultrasonic forceps devices operates user input device (600) to control an ultrasonic forceps version of end effector (150), the control of the ultrasonic forceps version of end effector (150) may be more intuitive to the operator than the control might otherwise be if the operator were using a differently configured user input device (600).

As yet another merely illustrative alternative, user input device (600) may be preferable for use with versions of end effector (150) that are in the form of an RF electrosurgical sealing and cutting end effector, having a pair of jaws, a distally translating blade, and bipolar electrodes that are operable to apply RF energy to tissue. In such versions, trigger (602) may selectively actuate the jaws to a closed configuration by driving the translating blade distally. In addition, button (604) may selectively activate the electrodes to apply RE energy to tissue that is captured between the jaws. Those of ordinary skill in the art will recognize that, to the extent that user input device (600) is configured similar to a handle assembly of an electrosurgical instrument, this configuration may provide the operator with an intuitive, familiar "feel." In other words, when an operator who is experienced using conventional electrosurgical instruments operates user input device (600) to control an electrosurgical sealing and cutting version of end effector (150), the control of the electrosurgical sealing and cutting version of end effector (150) may be more intuitive to the operator than the control might otherwise be if the operator were using a differently configured user input device (600).

III. Exemplary Clutch Systems

Figure 23:
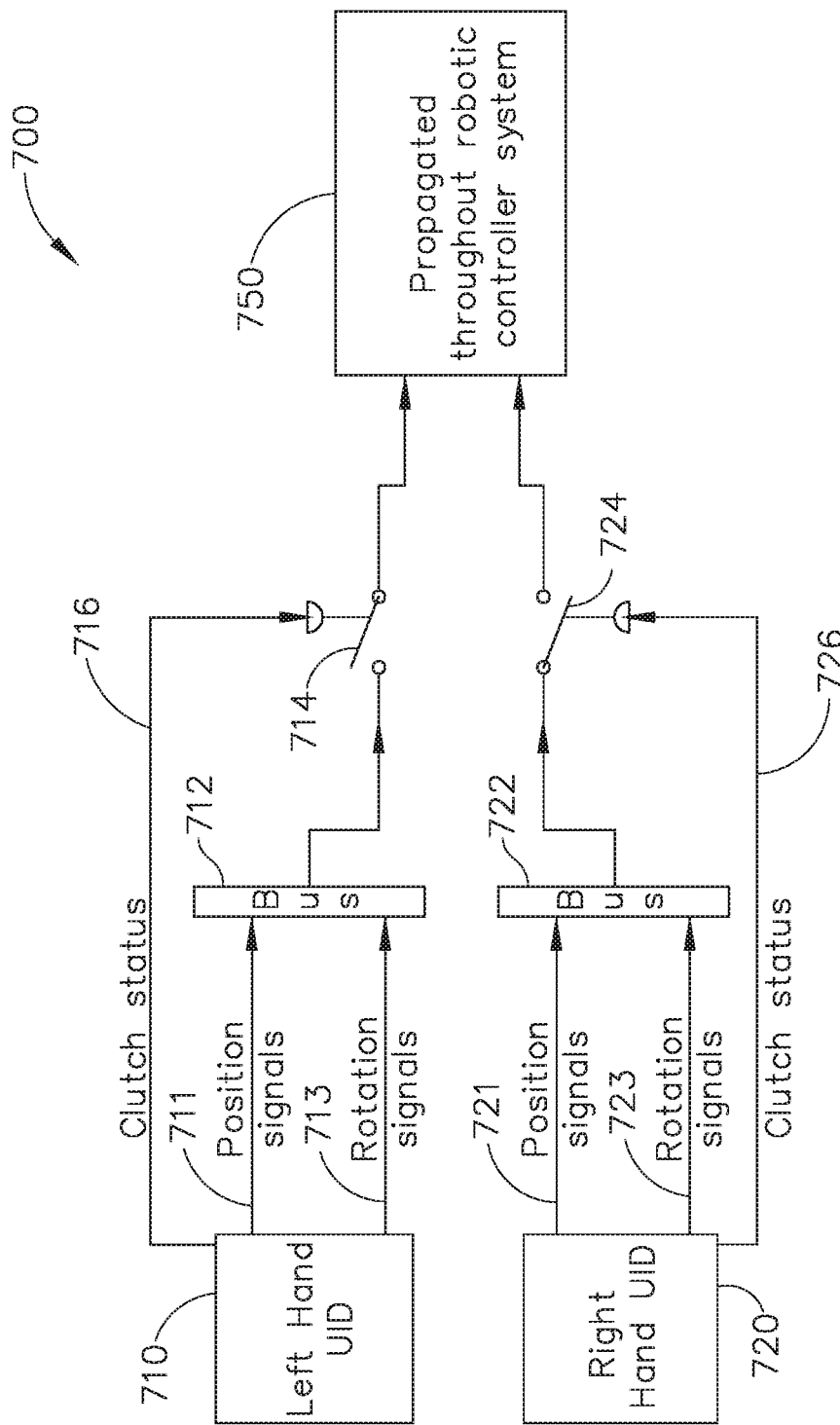
FIG. 23 depicts a schematic view of an exemplary clutch system that may selectively control when user input devices may communicate with the rest of the robotic surgical assembly of FIG. 1.

In some instances, it may be desirable to have a clutch switch that prevents control signals from being sent from a user input device assembly (22) to the rest of robotic surgical system (10) in the absence of one or more certain conditions. Preventing control signals from being sent unless a clutch switch is activated may ensure that an operator intends for movement of user input device assembly (22) to actually move a robotic arm or surgical instrument located at operation assembly (40). This may prevent unintentional movement of a robotic arm or surgical instrument by accidental movement of an input device assembly (22). While the clutch systems are described below in the context of input device assembly (22), it should be understood that the clutch systems described below may be used in combination with any of the various user input devices (100, 200, 300, 400, 500, 600) described herein, among other kinds of user input devices, FIG. 23 shows an exemplary clutch system (700). Exemplary clutch system (700) includes a left hand user input device (710) and a right hand user input device (720), each of which are connected to a respective bus unit (712, 722) and a respective switch assembly (714, 724). Switch assemblies (714, 724) are further in communication with a processing device (750). Processing device (750) may be configured and operable like processing device (26) described above. Thus, control signals may be communicated through processing device (750) to ultimately control one or more robotic arms and associated surgical instruments at a corresponding robotic actuation assembly (48).

Each user input device (710, 720) includes a respective clutch feature (not shown) that is operable to generate a clutch signal. By way of example only, these clutch features may include buttons, switches, capacitive sensors, or any other suitable kind of features. In some versions, the clutch features will be automatically actuated or activated simply by the operator's grasping of user input devices (710, 720), such that the operator does not need to separately or intentionally actuate or activate the clutch feature. In some other versions, the clutch feature is not necessarily actuated or activated simply by the operator's grasping of user input devices (710, 720), such that the operator does need to separately or intentionally actuate or activate the clutch feature. In either case, when the clutch features are actuated or activated, a clutch signal is communicated along the corresponding clutch line (716, 726). It should be understood that, when a clutch signal is being communicated along a clutch line (716, 726), this clutch signal indicates that the operator is actively grasping the corresponding user input device (710, 720). Similarly, when a clutch signal is not being communicated along a clutch line (716, 726), this absence of the clutch signal indicates that the operator is not actively grasping the corresponding user input device (710, 720). Various suitable components and configurations that may be incorporated into user input devices (710, 720) to provide clutch features will be apparent to those of ordinary skill in the art in view of the teachings herein.

Switch assemblies (714, 724) are configured to remain in an open state by default. Switch assemblies (714, 724) are further configured to transition to a closed state in response to the presence of a clutch signal along the corresponding clutch line (716, 726). Thus, when the operator is actively grasping a user input device (710, 720), the corresponding switch assembly (714, 724) will be in a closed state. However, when the operator is not actively grasping a user input device (710, 720), the corresponding switch assembly (714, 724) will be in an open state. While switch assemblies (714, 724) are shown as digital switches in the present example, it should be understood that switch assemblies (714, 724) may also be in the form of analog switch assemblies (714, 724) (e.g., including relays, etc.). Various components and configurations that may be used to form switch assemblies (714, 724) will be apparent to those of ordinary skill in the art in view of the teachings herein.

Bus units (712, 722) are configured to receive position signals (711, 721) and rotation signals (713, 723) of respective user input devices (710, 720). When clutch lines (716, 726) do not activate switch assemblies (714, 724), bus units (712, 722) will not be able to convey signals (711, 713, 721, 723) to processing device (750), and therefore robotic arms and surgical instruments will not move.

When switch assemblies (714, 724) connect bus units (712, 722) to processing device (750) by clutch lines (716, 726) being activated, bus units (712, 722) will be able to convey position signals (711, 721) and rotation signals (713, 723) to processing device (750) and therefore, robotic arms and surgical instruments will move. In the present example, clutch lines (716, 726) may be individually activated such that individual bus units (712, 722) may connect with processing device (750). Therefore, in the event that a. clutch signal is present on clutch line (716) but absent from clutch line (726), one user input device (710) may move a robotic arm and/or associated surgical instrument while the other user input device (720) is effectively locked out.

Figure 24:
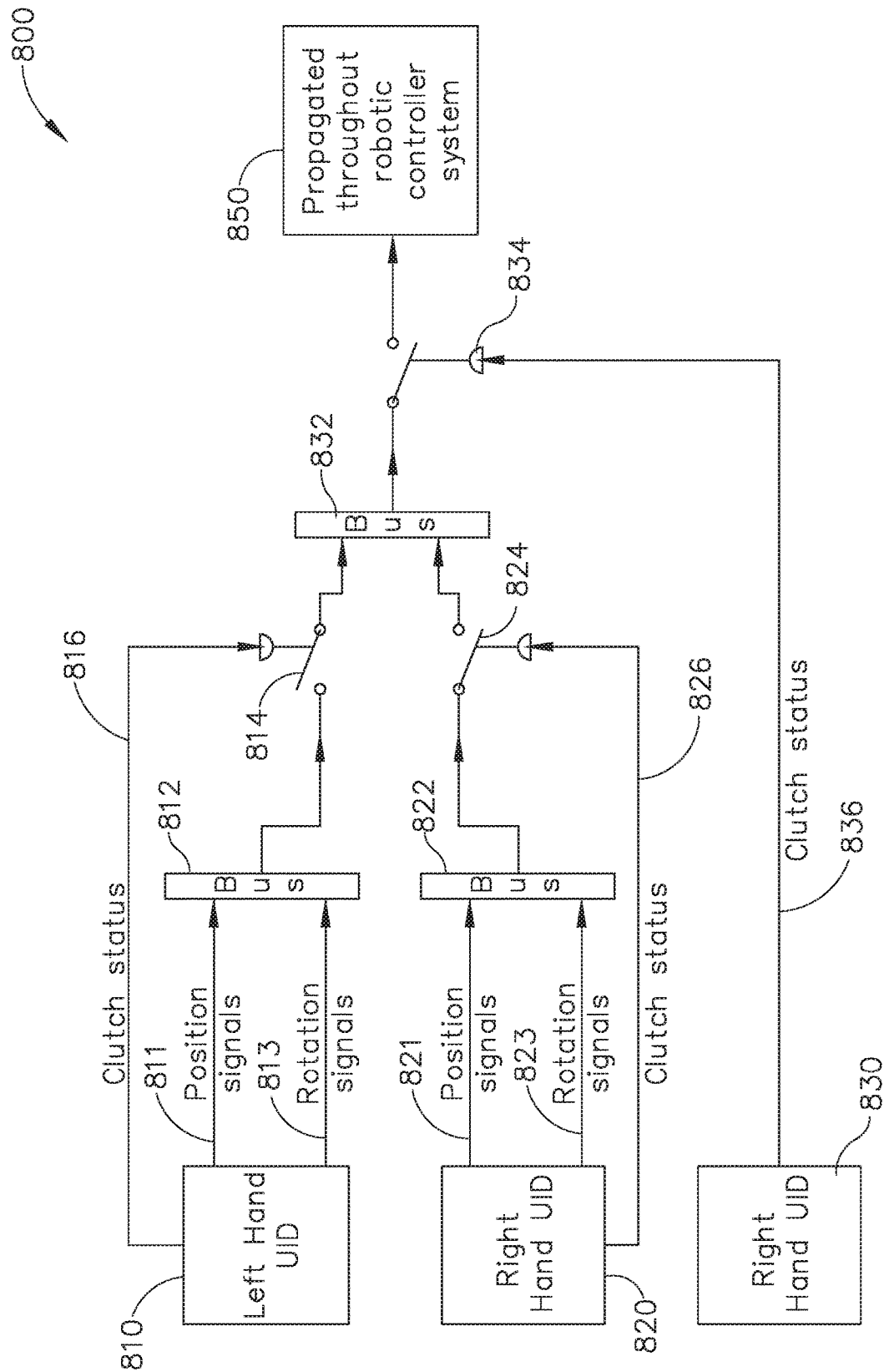
FIG. 24 depicts a schematic view of another exemplary clutch system that may selectively control when user input devices may communicate with the rest of the robotic surgical assembly of FIG. I.

FIG. 24 shows another exemplary clutch system (800) that is substantially similar to clutch system (700) described above, with differences elaborated below. In particular, clutch system (800) of this example includes a left hand user input device (810) and a right hand user input device (820), each having their own respective clutch features. Clutch system (800) of this example further includes bus units (812, 822), position signals (811, 821), rotational signals (813, 823), clutch lines (816, 826), and switch assemblies (814, 824) associated with each corresponding user input device (810, 820). It should be understood that the above-noted components of clutch system (800) are configured and operable just like left hand user input device (710), right hand user input device (720), bus units (712, 722), position signals (711, 721), rotational signals (713, 723), clutch lines (716, 726) and switch assemblies (714, 724) described above, respectively.

However, unlike clutch system (700), clutch system (800) of the present example also includes a bus unit (832) in communication with switch assemblies (814, 8724). Thus, when switch assemblies (814, 824) are in a closed state (based on clutch signals being present on clutch lines (816, 826)), control signals from user input devices (810, 820) may pass through to bus unit (832).

Clutch system (800) of the present example further includes a foot control device (830) with a clutch line (836) going to another switch assembly (834). Foot control device (830) is configured to generate a clutch signal, and communicate the clutch signal along clutch line (836), when an operator is actively stepping on foot control device (830). Switch assembly (834) is configured to transition between an open and closed state based on the presence of the clutch signal on clutch line (836). In particular, switch assembly (834) will be in a closed state when a clutch signal is present on clutch line (836); and in an open state when a clutch signal is not present on clutch line (836). While switch assembly (834) is shown as a digital switch in the present example, it should be understood that assembly (834) may also be in the form of an analog switch assembly (834) (e.g., including a relay, etc.). Various components and configurations that may be used to form switch assembly (834) will be apparent to those of ordinary skill in the art in view of the teachings herein.

Switch assembly (834) is further in communication with bus unit (832) and a processing device (850). Processing device (850) may be configured and operable like processing device (26) described above. Thus, control signals may be communicated through processing device (850) to ultimately control one or more robotic arms and associated surgical instruments at a corresponding robotic actuation assembly (48). It should be understood that control signals from user input devices (810, 820) will not be passed from bus unit (832) to processing device (850) unless switch assembly (834) is in a closed state based on the presence of a clutch signal from foot control (830). Therefore, foot control (930) acts as an additional safety switch for the rest of the clutch system (800). In other words, the operator must simultaneously actuate foot control (830) and the clutch feature of at least one user input device (810, 820) in order for the control signals from user input device (810, 820) to reach robotic actuation assembly (48).

While a foot control (830) is used to generate a third clutch signal external to user input devices (810, 820) in the present example, it should be understood that various other kinds of clutch input devices may be used to generate a third clutch signal external to user input devices (810, 820). By way of example only, an alternative clutch input device may include a switch that is activated by the operator's head (e.g., switch located in a piece of headgear worn by the operator, switch provided by sensing of operator's head within a predefined space, etc.), a proximity sensor (e.g., detecting presence of user input devices (810, 820) within a predefined space, etc.), and/or any other kind of clutch input device that is located external to user input devices (810, 820).

Figure 25:
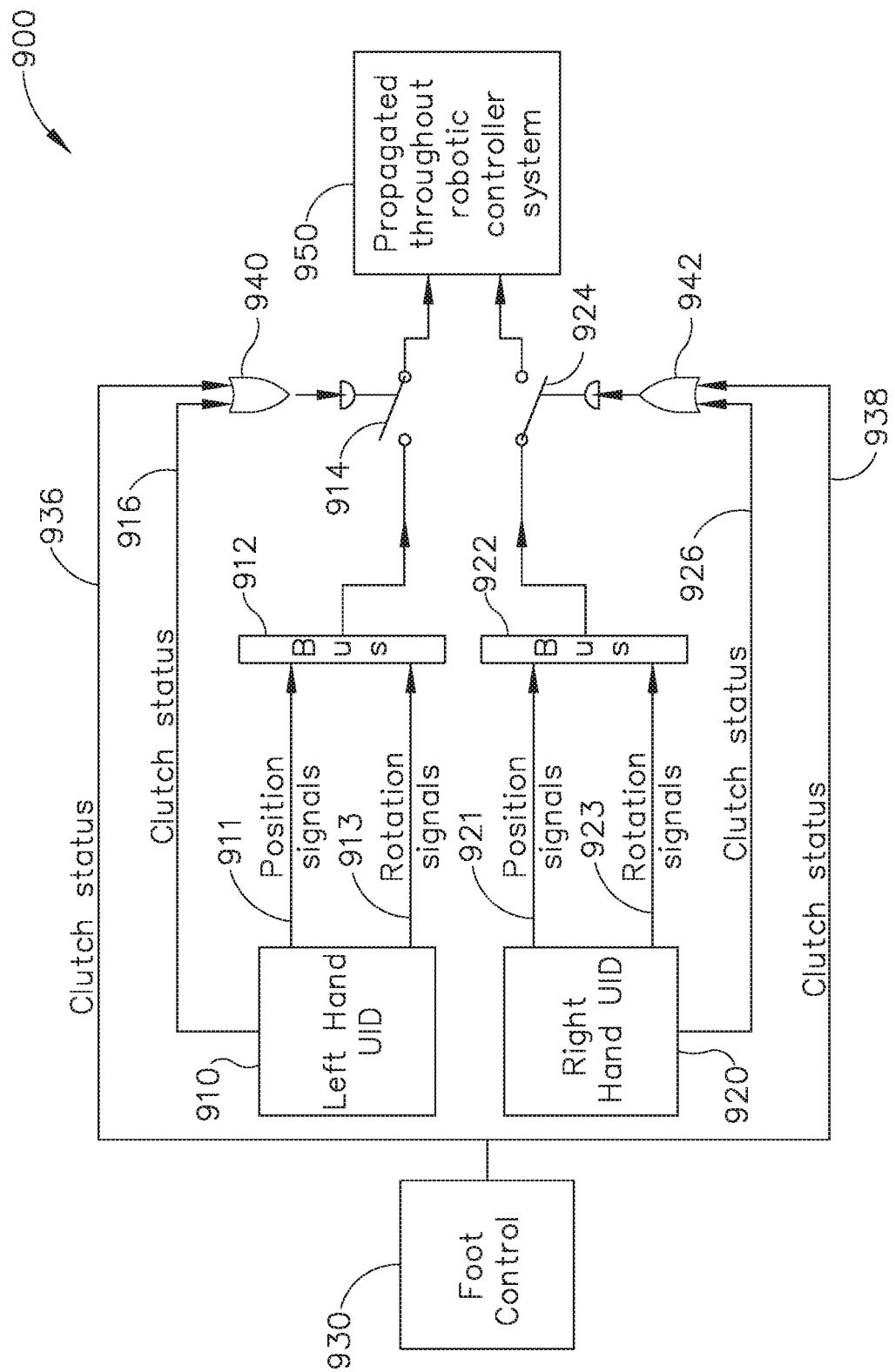
FIG. 25 depicts a schematic view of another exemplary clutch system that may selectively control when user input devices may communicate with the rest of the robotic surgical assembly of FIG. 1.

FIG. 25 shows another exemplary clutch system (900) that is substantially similar to clutch system (700) described above, with differences elaborated below. In particular, clutch system (900) of this example includes a left hand user input device (910) and a right hand user input device (920), each having their own respective clutch features. Clutch system (900) of this example further includes bus units (912, 922), position signals (911, 921), rotational signals (913, 923), clutch lines (916, 926), and switch assemblies (914, 924) associated with each corresponding user input device (910, 920), It should be understood that the above-noted components of clutch system (900) are configured and operable just like left hand user input device (710), right hand user input device (720), bus units (712, 722), position signals (711, 721), rotational signals (713, 723), clutch lines (716, 726), and switch assemblies (714, 724) described above, respectively, except for the differences noted below.

Unlike clutch system (700), in clutch system (900) of the present example clutch lines (916, 926) are in communication with corresponding OR gates (940, 942). Each OR gate (940, 942) is in communication with a corresponding switch assembly (914, 924). Each OR gate (940, 942) is in further communication with a corresponding clutch line (936, 938). Each clutch line (936, 938) is further in communication with a foot control device (930). Foot control device (930) is configured to generate a clutch signal, and communicate the clutch signal along clutch lines (938, 936), when an operator is actively stepping on foot control device (930).

OR gate (940) is configured to provide a switch closing signal to switch assembly (914) when a clutch signal is present on either or both of clutch line (916) or clutch line (936). When OR gate (940) provides a switch closing signal to switch assembly (914), switch assembly (914) transitions to a closed state. However, when OR gate (940) is not providing a switch closing signal to switch assembly (914), switch assembly (914) will remain in an open state. It should therefore be understood that switch assembly (914) will be in a closed state when the clutch feature of user input device (910) is being activated and/or when foot control device (930) is being actuated; but switch assembly (914) will be in an open state when the clutch feature of user input device (910) is not being activated and foot control device (930) is not being actuated.

Similarly, OR gate (942) is configured to provide a switch closing signal to switch assembly (924) when a clutch signal is present on either or both of clutch line (926) or clutch line (938). When OR gate (942) provides a switch closing signal to switch assembly (924), switch assembly (924) transitions to a closed state. However, when OR gate (942) is not providing a switch closing signal to switch assembly (924), switch assembly (924) will remain in an open state. It should therefore be understood that switch assembly (924) will be in a closed state when the clutch feature of user input device (920) is being activated and/or when foot control device (930) is being actuated; but switch assembly (924) will be in an open state when the clutch feature of user input device (920) is not being activated and foot control device (930) is not being actuated.

Switch assemblies (914) are further in communication with processing device (950). Processing device (950) may be configured and operable like processing device (26) described above. Thus, control signals may be communicated through processing device (950) to ultimately control one or more robotic arms and associated surgical instruments at a corresponding robotic actuation assembly (48). It should be understood that control signals from user input devices (910, 920) will not be passed to processing device (950) unless the corresponding switch assembly (914, 924) is in a closed state based on the presence of a clutch signal from either foot control (930) or the clutch feature of the corresponding user input device (910, 920).

While a foot control (930) is used to generate a third clutch signal external to user input devices (910, 920) in the present example, it should be understood that various other kinds of clutch input devices may be used to generate a third clutch signal external to user input devices (910, 920). By way of example only, an alternative clutch input device may include a switch that is activated by the operator's head (e.g., switch located in a piece of headgear worn by the operator, switch provided by sensing of operator's head within a predefined space, etc.), a proximity sensor (e.g., detecting presence of user input devices (910, 920) within a predefined space, etc.), and/or any other kind of clutch input device that is located external to user input devices (910, 920).

Figure 26:
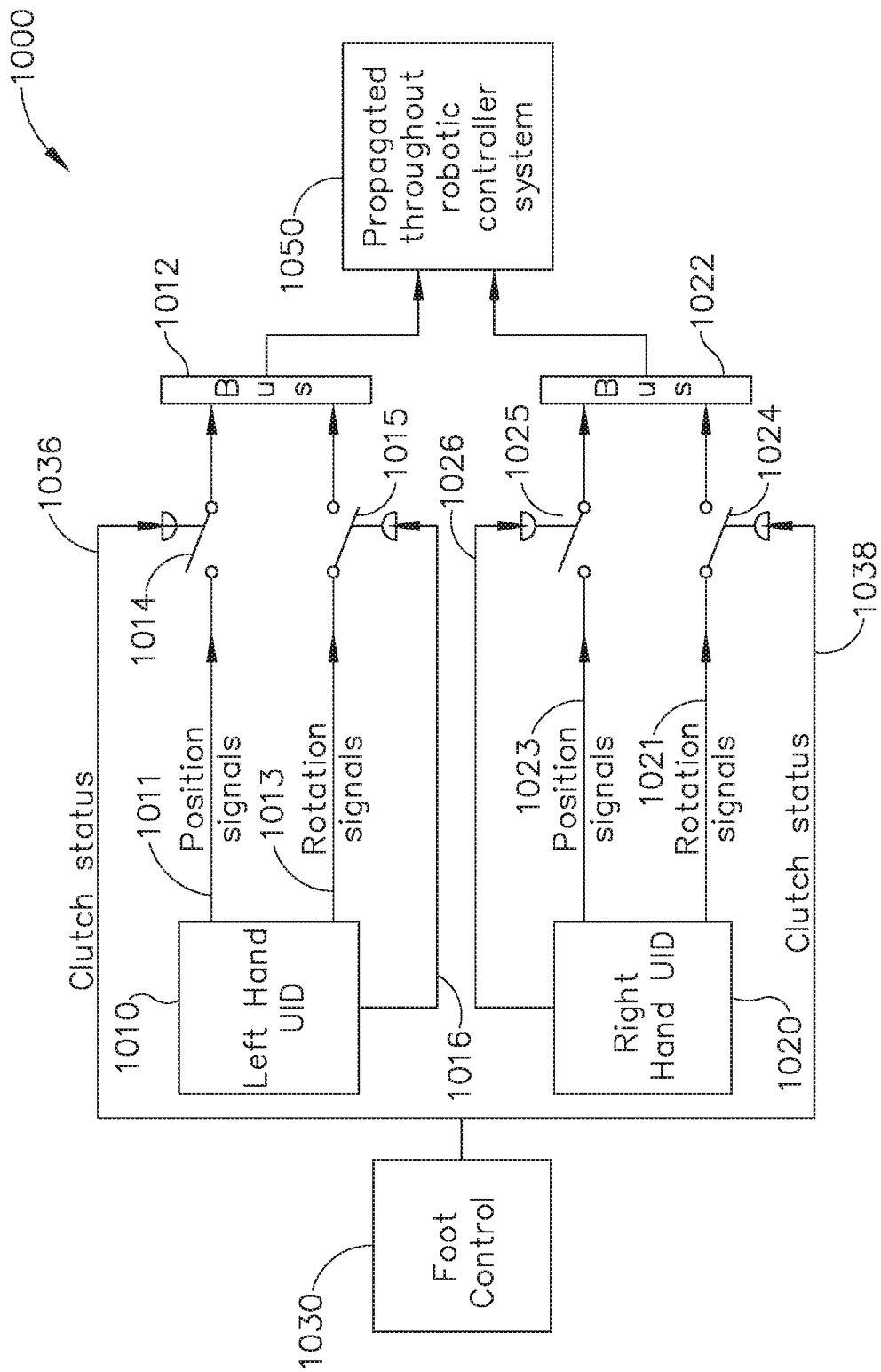
FIG. 26 depicts a schematic view of another exemplary clutch system that may selectively control when user input devices may communicate with the rest of the robotic surgical assembly of FIG. 1.

FIG. 26 shows another exemplary clutch system (1000) that is substantially similar to clutch system (700) described above, with differences elaborated below. In particular, clutch system (1000) of this example includes a left hand user input device (1010) and a right hand user input device (1020), each having their own respective clutch features. Clutch system (1000) of this example further includes bus units (1012, 1022), position signals (1011, 1021), rotational signals (1013, 1023), and clutch lines (1016, 1026) associated with each corresponding user input device (1010, 1020). It should be understood that the above-noted components of clutch system (1000) are configured and operable just like left hand user input device (710), right hand user input device (720), bus units (712, 722), position signals (711, 721), rotational signals (713, 723), and clutch lines (716, 726) described above, respectively, except for the differences noted below.

Unlike clutch system (700), clutch system (1000) of the present example has a pair of switch assemblies (1014, 1015) associated with user input device (1010) and a pair of switch assemblies (1024, 1025) associated with user input device (1020). Switch assembly (1014) is in communication with bus unit (1012) and a clutch line (1014); and is operable to transmit position signals (1011) to bus unit (1012) when switch assembly (1014) is in a closed state. Switch assembly (1015) is in communication with bus unit (1012) and a clutch line (1016); and is operable to transmit rotation signals (1013) to bus unit (1012) when switch assembly (1014) is in a closed state. Switch assembly (1025) is in communication with bus unit (1022) and a clutch line (1026); and is operable to transmit rotation signals (1023) to bus unit (1022) when switch assembly (1025) is in a closed state. Switch assembly (1024) is in communication with bus unit (1022) and a clutch line (1038); and is operable to transmit position signals (1021) to bus unit (1022) when switch assembly (1024) is in a closed state.

It should be understood that clutch signals will be communicated along clutch lines (1016, 1026) based on actuation of clutch features of corresponding user input devices (1010, 1020). It should also be understood that switch assembly (1015) will be in a closed state in response to a clutch signal on clutch line (1016), thereby permitting rotation signals (1013) to reach bus unit (1012); but switch assembly (1015) will be in an open state in the absence of a clutch signal on clutch line (1016), thereby preventing rotation signals (1013) from reaching bus unit (1012). Similarly, switch assembly (1025) will be in a closed state in response to a clutch signal on clutch line (1026), thereby permitting rotation signals (1023) to reach bus unit (1022); but switch assembly (1025) will be in an open state in the absence of a clutch signal on clutch line (1026), thereby preventing rotation signals (1023) from reaching bus unit (1022).

It should also be understood that switch assembly (1014) will be in a closed state in response to a clutch signal on clutch line (1036), thereby permitting position signals (1011) to reach bus unit (1012); but switch assembly (1014) will be in an open state in the absence of a clutch signal on clutch line (1014), thereby preventing position signals (1011) from reaching bus unit (1012). Similarly, switch assembly (1024) will be in a closed state in response to a clutch signal on clutch line (1036), thereby permitting position signals (1021) to reach bus unit (1022); but switch assembly (1024) will be in an open state in the absence of a clutch signal on clutch line (1038), thereby preventing position signals (1023) from reaching bus unit (1022).

Clutch system (1000) of the present example further includes a foot control device (1030) in communication with clutch lines (1036, 1038). Foot control device (1030) is configured to generate a clutch signal, and communicate the clutch signal along clutch lines (1036, 1038), when an operator is actively stepping on foot control device (1030). Thus, switch assemblies (1014, 1024) will each be in a closed state when a clutch signal is present on clutch lines (1036, 1038); and in an open state when a clutch signal is not present on clutch lines (1036, 1038).

Bus units (1012, 1022) are further in communication with a processing device (1050). Processing device (1050) may be configured and operable like processing device (26) described above. Thus, control signals may be communicated through processing device (1050) to ultimately control one or more robotic arms and associated surgical instruments at a corresponding robotic actuation assembly (48). It should be understood that rotation signals (1013, 1023) may not reach processing device (1050) unless the clutch features of the corresponding user input devices (1010, 1020) are actuated, regardless of whether foot control device (1030) is being actuated. In other words, the clutch feature of a user input device (1010, 1020) must be in an actuated state in order for rotation signals (1013, 1023) from that user input device (1010, 1020) to reach processing device (1050), regardless of whether foot control device (1030) is being actuated. In addition, position signals (1011, 1021) may not reach processing device (1050) unless foot control device (1030) is being actuated, regardless of whether clutch features of user input devices (1010, 1020) are being actuated. In other words, foot control device (1030) must be in an actuated state in order for position signals (1011, 1021) to reach processing device (1050), regardless of whether clutch features of user input devices (1010, 1020) are being actuated.

While clutch system (1000) of the present example provides selective clutching of position signals (1011, 1023) based solely on actuation of foot control device (1030), it should be understood that other operabilities of end effector (150) may be selectively clutched based solely on actuation of foot control device (1030). Similarly, while clutch system (1000) of the present example provides selective clutching of rotation signals (1013, 1021) based solely on actuation of clutch features of user input devices (1010, 1020), it should be understood that other operabilities of end effector (150) may be selectively clutched based solely on actuation of clutch features of user input devices (1010, 1020).

Figure 27:
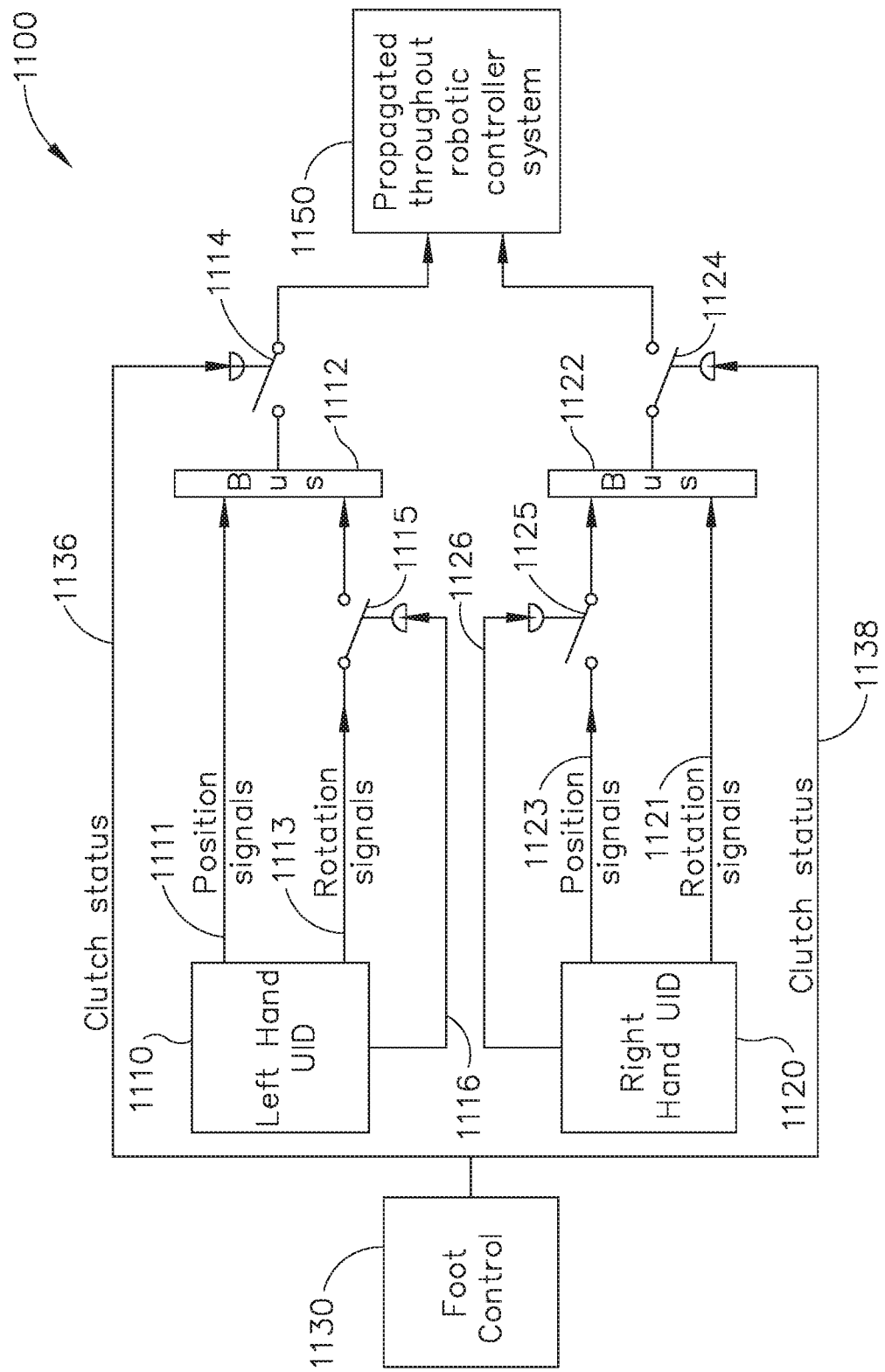
FIG. 27 depicts a schematic view of another exemplary clutch system that may selectively control when user input devices may communicate with the rest of the robotic surgical assembly of FIG. 1.

FIG. 27 shows another exemplary clutch system (1110) that is essentially a hybrid of clutch system (800) and clutch system (1000). Clutch system (1110) of this example comprises a left hand user input device (1110) and a right hand user input device (1120), each having their own respective clutch features (not shown), position signals (1111, 1121), rotation signals (1113, 1123), clutch lines (1116, 1126), bus units (1112, 1122), and switch assemblies (1114, 1115, 1124, 1125). Clutch system (1110) also includes a processing device (1150) and a foot control (1130) with clutch lines (1136, 1138); which are substantially similar to processing device (1050), foot control (1030), and clutch lines (1036, 1038) described above.

Switch assemblies (1115, 1125) of clutch system (1100) operate just like switch assemblies (1015, 1024) of clutch system (1000). In particular, when switch assembly (1115) receives a clutch signal along clutch line (1116), switch assembly (1115) is configured to pass rotation signals (1113) to bus unit (1112); but switch assembly (1115) is not configured to pass rotation signals (1113) to bus unit (1112) when switch assembly (1115) does not receive a clutch signal along clutch line (1116). Similarly, when switch assembly (1125) receives a clutch signal along clutch line (1126), switch assembly (1125) is configured to pass rotation signals (1123) to bus unit (1122); but switch assembly (1125) is not configured to pass rotation signals (1123) to bus unit (1122) when switch assembly (1125) does not receive a clutch signal along clutch line (1126).

Unlike clutch system (1000), and more like clutch system (800), in clutch system (1100) of the present example (800), switch assemblies (1114, 1124) are located downstream of bus units (1112, 1122). Switch assemblies (1114, 1124) are configured to transition to a closed state in response to a clutch signal on clutch lines (1136, 1138); but remain in an open state in the absence of a clutch signal on clutch lines (1136, 1138). Clutch lines (1136, 1138) are in communication with a foot control device (1130), which is configured to generate the clutch signal, and communicate the clutch signal along clutch lines (1136, 1138), when an operator is actively stepping on foot control device (1130). When switch assembly (1114) is in a closed state based on actuation of foot control device (1130) control signals from user input device (1110) may reach processing device (1150); but control signals from user input device (1110) may not reach processing device (1150) when foot control device (1130) is in a non-actuated state. Similarly, when switch assembly (1124) is in a closed state based on actuation of foot control device (1130) control signals from user input device (1120) may reach processing device (1150); but control signals from user input device (1120) may not reach processing device (1150) when foot control device (1130) is in a non-actuated state.

Processing device (1150) may be configured and operable like processing device (26) described above. Thus, control signals may be communicated through processing device (1150) to ultimately control one or more robotic arms and associated surgical instruments at a corresponding robotic actuation assembly (48). It should be understood that no control signals from user input devices (1110, 1120) may reach processing device (1150) unless foot control device (1130) is being actuated. When foot control device (1130) is being actuated, processing device (1150) may receive at least some control signals from user input devices (1110, 1120). In particular, assuming foot control device (1130) is being actuated, processing device (1150) may receive only position signals (1111) from user input device (1110) when the clutch feature of user input device (1110) is in a non-actuated state; and may further receive rotation signals (1113) from user input device (1110) when the clutch feature of user input device (1110) is in an actuated state. Similarly, and again assuming foot control device (1130) is being actuated, processing device (1150) may receive only position signals (1121) from user input device (1120) when the clutch feature of user input device (1120) is in a non-actuated state; and may further receive rotation signals (1123) from user input device (1120) when the clutch feature of user input device (1120) is in an actuated state.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A robotic surgical system comprising: (a) a robotic surgical assembly comprising: (i) a robotic actuation assembly comprising a robotic arm, (ii) a processing device configured to instruct the robotic actuation assembly to perform a task based on a set of instructions, and (iii) a first communication device in communication with the processing device, wherein the first communication device is operable to transfer the set of instructions to the processing device; and (b) a control assembly comprising: (i) a second communication device operable to communicate the set of instructions to the first communication device, and (ii) a user input device assembly configured to selectively establish communication with the second communication device through a third communication device, wherein the user input device assembly is configured to generate the set of instructions and send the set of instruction to the second communication device when in communication with the second communication device, wherein at least a portion of the instructions are based on positioning of the user input device within three-dimensional space.

Example 2

The robotic surgical system of Example 1, wherein the user input device further comprises a wireless communication device configured to establish selective communication with the second communication device.

Example 3

The robotic surgical system of any one or more of Examples 1 through 2, wherein the user input device further comprises a position sensor assembly configured to spatially locate the user input device assembly and generate the set of instructions based on the spatial location of the user input device.

Example 4

The robotic surgical system of Example 3, wherein the position sensor is configured to determine a rotational position of the user input device and generate a set of instructions based on the rotational position of the user input device.

Example 5

The robotic surgical system of Example 4, wherein the position sensor is selectively detachable from the rest of the user input device.

Example 6

The robotic surgical system of any one or more of Examples 1 through 5, wherein the user input device comprises an egg-shaped body.

Example 7

The robotic surgical system of any one or more of Examples 1 through 5, wherein the user input device further comprises a pistol grip body.

Example 8

The robotic surgical system of Example 7, wherein the user input device further comprises a pair of pincher paddles configured to pivot toward and away from each other, wherein the set of instructions is based on the distance between the pair of pincher paddles.

Example 9

The robotic surgical system of Example 8, further comprising a trigger, wherein the set of instructions is based on whether the trigger is activated,

Example 10

The robotic surgical system of any one or more of Examples 7 through 9, wherein the user input device further comprises a rotating knob, wherein the set of instructions is based on a rotational placement of the rotating knob.

Example 11

The robotic surgical system of any one or more of Examples 1 through 5, wherein the user input device comprises a body comprising a first grip and a handle comprising a second grip, wherein the handle in pivotally connected to the body.

Example 12

The robotic surgical system of Example 11, further comprising a rotational sensor configured to measure an angle defined by the handle and the body.

Example 13

The robotic surgical system of Example 12, wherein the set of instructions is based on a reading of the rotational sensor.

Example 14

The robotic surgical system of Example 13, further comprising a button, wherein the set of instructions is based on whether or not the button is activated.

Example 15

The robotic surgical system of any one or more of Examples 1 through 5, wherein the user input device comprises a cylindrical body and a plurality of linkage buttons circumferentially encompassing the cylindrical body.

Example 16

The robotic surgical system of Example 15, wherein the plurality of linkage buttons are connected to a sled, wherein the sled is configured to longitudinally slide relative to cylindrical body in response to activation of linkage buttons, wherein the set of instructions is based on a longitudinal displacement of the sled relative to the cylindrical body.

Example 17

The robotic surgical system of Example 16, further comprising an actuator sensor, wherein the sled is configured to activate the actuator sensor, wherein the set of instructions is based on the activation of the actuator sensor.

Example 18

The robotic surgical system of any one or more of Examples I through 17, wherein the control assembly further comprises a viewing screen.

Example 19

A robotic surgical system comprising: (a) a robotic surgical assembly comprising: (i) a robotic actuation assembly comprising: (A) a robotic arm, and (B) a surgical instrument attached to the robotic arm, wherein the robotic arm is configured to move the surgical instrument, (ii) a processing device configured to instruct the robotic actuation assembly to perform a task based on a set of instructions, and (iii) a first communication device in communication with the processing device, wherein the first communication device is operable to transfer the set of instructions to the processing device; and (b) a control assembly comprising: (i) a second communication device operable to communicate the set of instructions to the first communication device, and (ii) a user input device assembly configured to selectively and wirelessly establish communication with the second communication device, wherein the user input device assembly is configured to generate the set of instructions and send the set of instruction to the second communication device when in communication with the second communication device.

Example 20

A robotic surgical system comprising: (a) a robotic arm; (b) a processing device in communication with the robotic arm, wherein the processing device is configured to deliver a position signal and a rotation signal to the robotic arm; and (c) a clutch assembly configured to selectively deliver the position signal and the rotation signal to the robotic arm, wherein the clutch assembly comprises: (i) a user input device configured to generate the position signal and the rotation signal, (ii) a bus unit configured to store the position signal and the rotation signal, and (iii) a clutching switch configured to selectively release the position signal and the rotation signal from the bus unit to the processing device.

IV. Miscellaneous

It should be understood that the teachings herein may be readily combined with the teachings of U.S. patent application Ser. No. 15/282,353, entitled "System and Method of Converting User Input into Motion of a Surgical Instrument via a Robotic Surgical System," filed Sep. 30, 2016, now U.S. Pat. No. 10,052,164, issued Aug. 21, 2018, the disclosure of which is incorporated by reference herein. Various suitable ways in which the teachings herein may be combined with the teachings of U.S. Pat. No. 10,052,164 will be apparent to those of ordinary skill in the art in view of the teachings herein.

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A robotic surgical system, comprising:
   (a) a robotic surgical assembly, wherein the robotic surgical assembly comprises a robotic actuation assembly configured perform a task based on a set of instructions; and
   (b) a control assembly configured to generate the set of instructions and communicate the set of instructions to the robotic surgical assembly, wherein the control assembly comprises a user input device, wherein the user input device comprises a position sensing assembly configured to generate at least a portion of the set of instructions based on the positioning of the position sensing assembly within three-dimensional space.

2. The robotic surgical system of claim 1, wherein the robotic actuation assembly further comprises a robotic arm.

3. The robotic surgical system of claim 1, wherein the robotic surgical assembly further comprises a processing device configured to instruct the robotic actuation assembly based on the set of instructions.

4. The robotic surgical system of claim 3, wherein the robotic surgical assembly further comprises a first communication device in communication with the processing device, wherein the first communication device is operable to transfer the set of instructions to the processing device.

5. The robotic surgical system of claim 1, wherein the control assembly further comprises a communication device operable to communicate the set of instructions to the robotic actuation assembly.

6. The robotic surgical system of claim 5, wherein the user input device comprises a wireless communication device configured to establish communication with the communication device of the control assembly.

7. The robotic surgical system of claim 6, wherein the wireless communication device is in communication with the position sensing assembly via a wired communication.

8. The robotic surgical system of claim 1, wherein the user input device is configured to selectively establish communication with the robotic surgical assembly.

9. The robotic surgical system of claim 1, wherein the position sensing assembly is selectively detachable from the rest of the user input device.

10. The robotic surgical system of claim 1, wherein the user input device further comprises a trigger configured to generate at least a portion of the set of instructions.

11. The robotic surgical system of claim 1, wherein the user input device comprises a button configured to generate at least a portion of the set of instructions.

12. The robotic surgical system of claim 1, wherein the user input device comprises a pair of paddle buttons.

13. The robotic surgical system of claim 12, wherein the user input assembly further comprises a sensor assembly configured to determine a distance between the pair of paddle buttons.

14. The robotic surgical system of claim 1, wherein the user input assembly comprises a pivoting handle configured to generate at least a portion of the set of instructions.

15. A robotic surgical system, comprising:
(a) a robotic surgical assembly, wherein the robotic surgical assembly comprises a robotic actuation assembly configured perform a task based on a set of instructions;
(c) a communication assembly configured to communicate the set of instructions to the robotic actuation assembly; and
(b) a control assembly configured to generate the set of instructions and communication the set of instructions to the communication assembly, wherein the control assembly comprises a user input device, wherein the user input device comprises a position sensing assembly configured to generate at least a portion of the set of instructions based on the positioning of the position sensing assembly within three-dimensional space.

16. The robotic surgical system of claim 15, wherein communication assembly comprises a server.

17. The robotic surgical system of claim 15, wherein the communication assembly is in wireless communication with both the control assembly and the robotic surgical assembly.

18. The robotic surgical system of claim 15, wherein the position sensing assembly comprises an accelerometer.

19. The robotic surgical system of claim 15, wherein the position sensing assembly comprises a coil.

20. A robotic surgical system, comprising:
(a) a robotic surgical assembly, wherein the robotic surgical assembly comprises a robotic actuation assembly configured perform a task based on a set of instructions;
(b) a user input device configured to generate the set of instructions and communicate the set of instructions to the robotic surgical assembly, wherein the user input device comprises a position sensing assembly configured to generate at least a portion of the set of instructions based on the positioning of the position sensing assembly within three-dimensional space.

* * * * *